United States Patent
Lin et al.

(10) Patent No.: US 7,979,107 B2
(45) Date of Patent: Jul. 12, 2011

(54) SYSTEM AND METHOD FOR DIFFERENTIATION OF NORMAL AND MALIGNANT IN VIVO LIVER TISSUES

(75) Inventors: Wei-Chiang Lin, Miami, FL (US); Steven A. Toms, Shaker Heights, OH (US); Anita Mahadevan-Jansen, Nashville, TN (US); Ravi S. Chari, Nashville, TN (US)

(73) Assignees: Vanderbilt University, Nashville, TN (US); Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 12/537,008

(22) Filed: Aug. 6, 2009

(65) Prior Publication Data

US 2009/0292211 A1  Nov. 26, 2009

Related U.S. Application Data

(60) Division of application No. 10/955,331, filed on Sep. 30, 2004, now abandoned, which is a continuation-in-part of application No. 10/613,225, filed on Jul. 3, 2003, now abandoned, and a continuation-in-part of application No. PCT/US03/31163, filed on Sep. 30, 2003.

(60) Provisional application No. 60/394,217, filed on Jul. 5, 2002, provisional application No. 60/415,282, filed on Sep. 30, 2002, provisional application No. 60/507,358, filed on Sep. 30, 2003.

(51) Int. Cl.
*A61B 5/05* (2006.01)
(52) U.S. Cl. .......... 600/407; 600/473; 600/476; 356/73; 356/318
(58) Field of Classification Search ................. 600/407, 600/473, 476; 356/73, 318
See application file for complete search history.

(56) References Cited

U.S. PATENT DOCUMENTS 4,017,192 A   4/1977 Rosenthal
(Continued)

OTHER PUBLICATIONS

Mourant et al., "Spectroscopic Diagnosis of Bladder Cancer with Elastic Light Scattering." 1995. Lasers in Surgery and Medicine. Volume 17. pages 350-357.*

(Continued)

*Primary Examiner* — Brian Casler
*Assistant Examiner* — James Kish
(74) *Attorney, Agent, or Firm* — Morris Manning Martin LLP; Tim Tingkang Xia, Esq.

(57) ABSTRACT

A method for differentiating malignant in vivo liver tissues from normal in vivo liver tissues of a living subject includes the steps of: (a) illuminating a first area and a second area of in vivo liver tissues of the living subject with a first excitation light, (b) measuring an intensity of fluorescent light emitted from each of the first area and the second area of in vivo liver tissues in response to the first excitation light as a function of wavelength so as to obtain a first and a second fluorescent spectra, respectively, (c) illuminating the first area and the second area of in vivo liver tissues with a second excitation light, (d) measuring an intensity of diffuse light reflected by each of the first area and the second area of in vivo liver tissues in response to the second excitation light as a function of wavelength so as to obtain a first and a second diffused reflectance spectra, respectively, and (e) identifying one of the first area and the second area of in vivo liver tissues as malignant liver tissues and the other one of the first area and the second area of in vivo liver tissues as normal liver tissues, by comparing the first fluorescence spectrum and the second florescence spectrum, and comparing the first diffused reflection spectrum and the second diffused reflection spectrum.

10 Claims, 13 Drawing Sheets

(a)

(b)

U.S. PATENT DOCUMENTS

| | | | |
|---|---|---|---|
| 4,397,314 A | 8/1983 | Vaguine | |
| 4,930,516 A | 6/1990 | Alfano et al. | |
| 4,961,422 A | 10/1990 | Marchosky et al. | |
| 4,967,745 A | 11/1990 | Hayes et al. | |
| 5,122,137 A | 6/1992 | Lennox | |
| 5,131,398 A | 7/1992 | Alfano et al. | |
| 5,197,466 A | 3/1993 | Marchosky et al. | |
| 5,222,953 A | 6/1993 | Dowlatshahi | |
| 5,303,026 A * | 4/1994 | Strobl et al. | 356/318 |
| 5,348,018 A | 9/1994 | Alfano et al. | |
| 5,349,954 A | 9/1994 | Tiemann et al. | |
| 5,452,723 A * | 9/1995 | Wu et al. | 600/342 |
| 5,467,767 A | 11/1995 | Alfano et al. | |
| 5,527,349 A | 6/1996 | Landry et al. | |
| 5,569,240 A | 10/1996 | Dowlatshahi et al. | |
| 5,660,181 A | 8/1997 | Ho et al. | |
| 5,672,173 A | 9/1997 | Gough et al. | |
| 5,672,174 A | 9/1997 | Gough et al. | |
| 5,699,798 A | 12/1997 | Hochman et al. | |
| 5,713,364 A * | 2/1998 | DeBaryshe et al. | 600/476 |
| 5,728,143 A | 3/1998 | Gough et al. | |
| 5,782,827 A | 7/1998 | Gough et al. | |
| 5,800,350 A | 9/1998 | Coppleson et al. | |
| 5,800,484 A | 9/1998 | Gough et al. | |
| 5,807,395 A | 9/1998 | Mulier et al. | |
| 5,810,804 A | 9/1998 | Gough et al. | |
| 5,813,987 A | 9/1998 | Modell et al. | |
| 5,827,276 A | 10/1998 | LeVeen et al. | |
| 5,849,595 A | 12/1998 | Alfano et al. | |
| 5,863,290 A | 1/1999 | Gough et al. | |
| 5,913,855 A | 6/1999 | Gough et al. | |
| 5,925,042 A | 7/1999 | Gough et al. | |
| 5,928,229 A | 7/1999 | Gough et al. | |
| 5,935,123 A | 8/1999 | Edwards et al. | |
| 5,951,547 A | 9/1999 | Gough et al. | |
| 5,954,655 A | 9/1999 | Hussman | |
| 5,980,517 A | 11/1999 | Gough | |
| 5,987,346 A | 11/1999 | Benaron et al. | |
| 6,008,889 A * | 12/1999 | Zeng et al. | 356/73 |
| 6,039,731 A | 3/2000 | Taylor et al. | |
| 6,053,937 A | 4/2000 | Edwards et al. | |
| 6,059,780 A | 5/2000 | Gough et al. | |
| 6,071,280 A | 6/2000 | Edwards et al. | |
| 6,080,150 A | 6/2000 | Gough | |
| 6,090,105 A | 7/2000 | Zepeda et al. | |
| 6,113,593 A | 9/2000 | Tu et al. | |
| 6,167,297 A | 12/2000 | Benaron | |
| 6,235,023 B1 | 5/2001 | Lee et al. | |
| 6,241,725 B1 | 6/2001 | Cosman | |
| 6,258,576 B1 * | 7/2001 | Richards-Kortum et al. | 435/40.52 |
| 6,309,352 B1 | 10/2001 | Oraevsky et al. | |
| 6,312,426 B1 | 11/2001 | Goldberg et al. | |
| 6,330,478 B1 | 12/2001 | Lee et al. | |
| 6,336,904 B1 | 1/2002 | Nikolchev | |
| 6,337,998 B1 | 1/2002 | Behl et al. | |
| 6,377,841 B1 | 4/2002 | Lin et al. | |
| 6,377,842 B1 | 4/2002 | Pogue et al. | |
| 6,471,698 B1 | 10/2002 | Edwards et al. | |
| 6,500,175 B1 | 12/2002 | Gough et al. | |
| 6,537,211 B1 | 3/2003 | Wang et al. | |
| 6,551,311 B2 | 4/2003 | Lee et al. | |
| 6,569,159 B1 | 5/2003 | Edwards et al. | |
| 6,605,085 B1 | 8/2003 | Edwards | |
| 6,622,731 B2 | 9/2003 | Daniel et al. | |
| 2002/0026127 A1 * | 2/2002 | Balbierz et al. | 600/567 |
| 2003/0013973 A1 * | 1/2003 | Georgakoudi et al. | 600/473 |
| 2003/0170898 A1 | 9/2003 | Gundersen et al. | |
| 2004/0054270 A1 | 3/2004 | Pewzner et al. | |

OTHER PUBLICATIONS

Wosikowski et al., WK175, a Novel Antitumor Agent, Decreases the Intracellular Nicotinamide Adenine Dinucleaotide Concentration and Induces the Apoptotic Cascade in Human Leukemia Cells, Feb. 15, 2002, Cancer Reasearch 62, pp. 1057-1062.

Asali et al., Use of NAD(P)H-fluorescence for Monitoring the Response of Starved Cells of Catharanthus Roseus in Suspension to Metabolic Perturbations, 1992, Jounral of Biotechnology, 23, pp. 83-94.

Sorenson et al., Analysis of Events Associated With Cell Cycle Arrest at G2 Phase and Cell Death Induced by Cisplatin, May 2, 1990, J. Natl. Cancer Inst., vol. 82, No. 9, pp. 749-755.

* cited by examiner

SYSTEM AND METHOD FOR DIFFERENTIATION OF NORMAL AND MALIGNANT IN VIVO LIVER TISSUES

CROSS-REFERENCE TO RELATED PATENT APPLICATION

This application is a divisional application of, and claims benefit of U.S. patent application Ser. No. 10/955,331, filed Sep. 30, 2004, now abandoned entitled "METHODS AND APPARATUS FOR OPTICAL SPECTROSCOPIC DETECTION OF CELL AND TISSUE DEATH," by Wei-Chiang Lin, Steven A. Toms, Anita Mahadevan-Jansen, and Ravi S. Chari, the disclosure of which is hereby incorporated herein in its entirety by reference. Application Ser. No. 10/955,331 is a continuation-in-part of U.S. patent application Ser. No. 10/613,225, filed Jul. 3, 2003, now abandoned entitled "APPARATUS AND METHODS OF DETECTION OF RADIATION INJURY USING OPTICAL SPECTROSCOPY," by Wei-Chiang Lin, Steven A. Toms, Anita Mahadevan-Jansen, Paul J. Phillips, Mahlon Johnson, and Robert J. Weil, the disclosure for which is hereby incorporated herein by reference in its entirety, which itself claims the benefit, pursuant to 35 U.S.C. §119(e), of provisional U.S. patent application Ser. No. 60/394,217, which was filed on Jul. 5, 2002, entitled "APPARATUS AND METHODS OF DETECTION OF RADIATION INJURY USING OPTICAL SPECTROSCOPY," by Wei-Chiang Lin, Steven A. Toms, Anita Mahadevan-Jansen, Paul J. Phillips, Mahlon Johnson, and Robert J. Weil, which is incorporated herein by reference in its entirety. Application Ser. No. 10/955,331 also is a continuation-in-part of PCT patent application Serial No. PCT/US2003/031163, filed Sep. 30, 2003, entitled "OPTICAL APPARATUS FOR GUIDED LIVER TUMOR TREATMENT AND METHODS," by Wei-Chiang Lin, William C. Chapman, and Anita Mahadevan-Jansen, the disclosure for which is hereby incorporated herein by reference in its entirety, which itself claims the benefit, pursuant to 35 U.S.C. §119(e), of provisional U.S. patent application Ser. No. 60/415,282, filed Sep. 30, 2002, entitled "OPTICAL APPARATUS FOR GUIDED LIVER TUMOR TREATMENT AND METHODS," by Wei-Chiang Lin, William C. Chapman, and Anita Mahadevan-Jansen, which is incorporated herein by reference in its entirety. Application Ser. No. 10/955,331 further claims the benefit, pursuant to 35 U.S.C. §119(e), of provisional U.S. patent application Ser. No. 60/507,358, filed Sep. 30, 2003, entitled "METHODS AND APPARATUS FOR OPTICAL SPECTROSCOPIC DETECTION OF CELL AND TISSUE DEATH," by Wei-Chiang Lin, Steven A. Toms, Anita Mahadevan-Jansen, and Ravi S. Chari, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

The present invention generally relates to tissue diagnosis, and in particular to the utilization of optical spectroscopy for cell and/or tissue death process detection, tissue discrimination, and surgical guidance.

BACKGROUND OF THE INVENTION

Cell death often refers to a situation where the cell is unable to maintain homeostasis from the environment. A tissue is an aggregation of morphologically similar cells and associated intercellular matter, and experiences death if the cells forming the tissue die. There are two distinct types of prelethal phases: oncosis and apoptosis. Oncosis of cells usually follows a variety of injuries, such as toxins and hyperthermia. Many of these injuries destroy adenosine triphosphate (hereinafter "ATP") synthesis and plasma membrane of cells. The lack of ATP and/or cell membrane integrity leads to imbalance in ion, e.g., $Na^+$, influx and efflux, and hence cell death occurs. Apoptosis of cells, on the other hand, is a fundamental cellular process involving the programmed cell death in response to diverse signals such as limb and neural development, neurodegenerative diseases and during the cellular response to radiotherapy and chemotherapy. During apoptosis, nicotinamide adenine dinucleotide phosphate (hereinafter "NAD(P)H") levels drop as mitochondrial oxidation becomes uncoupled, cytochrome c is released, caspases are activated, deoxyribonucleic acid (hereinafter "DNA") fragmented and programmed cell death occurs.

In vitro, oncosis may be quantified by various histological techniques such as Live/Dead assay and NAD(P)H staining. In addition to requiring cell or tissue samples from the host, these histological procedures usually are complex and very time-consuming. In vitro, apoptosis may be quantified by a series of static changes in enzyme and biochemical markers, such as cytochrome c release, poly adenosine-diphosphate ribose polymerase (hereinafter "PARP") cleavage, and DNA fragmentation. These changes can be monitored in terms of a series of stains and/or reactions fixing the cells, by Apotag™, Hoescht 33258 stain, propidium iodide staining, and fluorescence activated cell sorter (hereinafter "FACS") analysis. Therefore, real time monitoring of the reaction cannot be performed, as the cell or tissue must be killed during the assay.

For in vivo animal testing of novel therapeutics for conditions such as neurodegenerative conditions and cancer, results are mostly based upon sacrificing the animals and performing necropsy and analysis via immunohistochemistry and other pathologic techniques. In certain cases, animal magnetic resonance imaging (hereinafter "MRI") may allow imaging of the lesion or structures involved with the disease process being studied. All of these techniques are costly, time consuming and labor intensive, and require the sacrifice of large numbers of animals in order to achieve meaningful results.

There are no current techniques available for real time monitoring of the cellular processes leading to cell death in the petri dish (in vitro) or in animal and human therapeutics trials (in vivo).

Optical spectroscopy, such as fluorescence and diffused reflectance spectra, has been shown capable of detecting subtle changes in both biochemical compositions and morphological characteristics of tissues associated with the progression of disease in near real time, where these differences can be used to detect tissue abnormalities and ultimately lead to optical tissue discrimination. Optical spectroscopy has been successfully applied to detect disorders of various organs such as cervix and skin both in vitro and in vivo. Several commercial systems are currently available for clinical diagnosis in the bronchus, cervix, etc. However, relatively few studies have addressed the diagnostic potential of optical spectroscopy in tumors, such as brain tumor and liver tumor. Particularly, optical spectroscopic characteristics of liver tissues have not yet been developed.

Cancers, such as liver cancers, pose a significant problem to public health worldwide. Selecting the best treatment for liver cancer depends on the physician being able to precisely identify the type, location, size and borders of the tumor or tumors. By matching that information to a variety of treatment possibilities and considering the benefits and limitations of each, the physician can select the best course of action. Surgical removal of liver cancer tumors is considered to be the most effective treatment for liver cancer. Unfortunately, about 70% of patients cannot have this surgery due to the size or location of the tumors or other health factors. Thermotherapies such as radio frequency ablation (hereinafter "RFA") and laser-induced thermotherapy are often considered as alternative treatments. Currently, all thermotherapy procedures suffer from the lack of an adequate feedback control system, making it difficult to know precisely when to cease coagulation.

Proper deployment of an ablation probe is the first requirement for achieving a successful and effective liver tumor ablation (i.e., using the minimum numbers of ablation to achieve a thermal coagulation zone larger than the tumor). Currently, ablation probe placement is approximately determined in accordance with palpation and freehand ultrasound imaging. The accuracy of this approach, unfortunately, is hindered by the limitations of tumor margins detection using tumor echogenicity and stiffness. Once the ablation probe is in place, clinicians usually conduct the ablation using a pre-determined power and therapeutic duration (i.e., heating time) and/or local temperature information to conduct thermotherapies for liver tumors. This practice often yields unsatisfying therapeutic outcomes due to the fact that tissue characteristics vary drastically from patient to patient. In addition, the dynamics of tissue characteristics, such as temperature-dependent tissue properties, further complicate the process of thermal coagulation of liver tissues. Since the coagulation zones are often not visible during thermotherapy, it is difficult, if not impossible, to precisely determine the endpoint of therapy. To avoid the undesired therapeutic consequences and to perform precise and effective ablation, an effective feedback control strategy is clearly needed. This feedback mechanism should provide an objective method of determining the ideal placement of the ablation probe, and an objective endpoint for thermotherapies of liver tumors.

Since thermal coagulation of tissues is an outcome of the interaction between heat and tissue components, it is obvious that local temperature can serve as a convenient metric for monitoring the progress of thermotherapies of liver tumors. This concept has been previously implemented using thermocouple measurements and intraoperative MRI (hereinafter "iMRI"). The translation of local temperature-time history into degree of local tissue thermal damage often requires the assistance of a thermal damage model based on rate process theory. In this model, tissue thermal damage is expressed as an Arrhenius integral that depends on tissue temperature-time history, a tissue-dependent frequency factor (A), and an activation energy barrier (Ea). As indicated by the model, the effectiveness of temperature-based tissue thermal damage assessment hinges on the accurate measurement of local temperature-time history, which is difficult to achieve with either thermocouples or iMRI. In addition, knowledge of A and Ea of tissues is largely unavailable. These limitations make temperature-based feedback control of thermotherapies of liver tumors less than optimal.

Therefore, a heretofore unaddressed need exists in the art to address the aforementioned deficiencies and inadequacies.

SUMMARY OF THE INVENTION

The present invention, in one aspect, relates to a method for detecting death process of a cell of a living subject. In one embodiment, the method includes the steps of illuminating the cell of the living subject with a coherent light, collecting fluorescent light returned from the illuminated cell of the living subject, identifying a NAD(P)H peak of a spectrum of the collected fluorescent light with a wavelength, $\lambda_{peak}$, and obtaining the intensity of the NAD(P)H peak of the spectrum of the collected fluorescent light substantially corresponding to the wavelength $\lambda_{peak}$. The method farther includes the step of repeating the illuminating, collecting, identifying, and obtaining steps at sequential stages until the intensity of the NAD(P)H peak of the spectrum at a current stage M is less than the intensity of the NAD(P)H peak of the spectrum at an earlier stage M−1, so as to detect death process of the cell of the living subject at the current stage M using the intensity of the NAD(P)H peak of the spectrum, where the stage M−1 is immediately prior to the current stage M, and M is an integer greater than 1. In one embodiment, the coherent light has a wavelength substantially at about 337 nm. The wavelength $\lambda_{peak}$ of the NAD(P)H peak is substantially at about 460 nm.

The cell of the living subject experiences apoptosis leading to death at the current stage M when the NAD(P)H peak intensity at the current stage M is less than the NAD(P)H peak intensity at the earlier stage M−1. In one embodiment, the cell of the living subject is native at a first stage and is subject to hyperthermia and/or cisplatin for various periods of time at the sequential stages.

In another aspect, the present invention relates to a method for detecting death process of a tissue of a living subject, wherein the tissue is an aggregation of morphologically similar cells and associated intercellular matter. In one embodiment, the method has the step of illuminating an area of the tissue of the living subject with a coherent light. The coherent light, in one embodiment, has a wavelength substantially at about 337 nm. The method further has the steps of collecting fluorescent light returned from the illuminated area of the tissue of the living subject, identifying a NAD(P)H peak of a spectrum of the collected fluorescent light with a wavelength, $\lambda_{peak}$, and obtaining the intensity of the NAD(P)H peak of the spectrum of the collected fluorescent light substantially corresponding to the wavelength speak The wavelength $\lambda_{peak}$ of the NAD(P)H peak is substantially at about 460 nm.

Moreover, the method has the step of repeating the illuminating, collecting, identifying, and obtaining steps at sequential stages until the intensity of the NAD(P)H peak of the spectrum at a current stage M is less than the intensity of the NAD(P)H peak of the spectrum at an earlier stage M−1, so as to detect death process of the tissue of the living subject at the current stage M using the intensity of the NAD(P)H peak of the spectrum. The stage M−1 is immediately prior to the current stage M, and M is an integer greater than 1. The illuminated area of the tissue of the living subject experiences apoptosis leading to death at the current stage M when the NAD(P)H peak intensity at the current stage M is less than the NAD(P)H peak intensity at the earlier stage M−1. In one embodiment, the tissue of the living subject is native at a first stage and is subject to hyperthermia and/or cisplatin for various periods of time at the sequential stages.

In yet another aspect, the present invention relates to an apparatus for detecting death process of at least one cell of a living subject. In one embodiment, the at least one cell of the living subject is separable from a tissue of a living subject. In another embodiment, the at least one cell of the living subject is associated with a tissue of a living subject.

In one embodiment, the apparatus has a light source that is adapted for emitting coherent light with a wavelength at least in a range of between 300 nm and 400 nm, and more preferably in a range of between 320 nm and 380 nm. In one embodiment, the light source includes a laser. Preferably, the laser has at least one wavelength substantially at about 337 nm. Furthermore, the apparatus has a fiber optical probe that is coupled with the light source and adapted for delivering the coherent light to the at least one cell of the living subject proximal to a working end of the fiber optical probe. Moreover, the apparatus has a detector coupled with the fiber optical probe so as to receive from the working end of the fiber optical probe fluorescent light returned from the at least one cell of the living subject in response to illumination by the coherent light and to provide a frequency spectrum of the returned fluorescent light. In one embodiment, the detector includes a spectrometer. Additionally, the apparatus has a controller coupled with the detector and programmed to identify a NAD(P)H peak of a frequency spectrum of the returned fluorescent light with a wavelength, $\lambda_{peak}$, and the corresponding intensity of the NAD(P)H peak of the frequency spectrum of the returned fluorescent light so as to detect death process of the illuminated at least one cell of the living subject. The programmed controller is utilized to identify the death of at least one cell of the living subject upon a detected change in the NAD(P)H peak. The wavelength $\lambda_{peak}$ of the NAD(P)H peak is substantially at about 460 nm.

In a further aspect, the present invention relates to a method for identifying an in vitro liver tissue of a living subject. In one embodiment, the method includes the steps of acquiring a fluorescence spectrum of an in vitro liver tissue to be identified, acquiring a diffused reflectance spectrum of the in vitro liver tissue, and identifying a first peak and a second peak of the fluorescence spectrum, and a spectral profile of the diffused reflectance spectrum in a predetermined wavelength region, respectively, so as to identify the in vitro liver tissue. The first peak of the fluorescence spectrum includes a first peak wavelength, $\lambda_1$, and a corresponding first peak intensity, $F(\lambda_1)$, and the second peak of the fluorescence spectrum includes a second peak wavelength, $\lambda_2$, and a corresponding second peak intensity, $F(\lambda_2)$. The spectral profile of the diffused reflectance spectrum includes a spectral shape and intensity, and the predetermined wavelength region is from about 600 nm to about 800 nm.

In one embodiment, the step of acquiring the fluorescence spectrum of the in vitro liver tissue includes the steps of illuminating an area of the in vitro liver tissue with an excitation light, and collecting fluorescent light returned from the illuminated area of the in vitro liver tissue. The excitation light can be a coherent light or a non-coherent light as long as it has adequate wavelength and intensity so as to induce fluorescent emission from tissue. The step of acquiring the diffused reflectance spectrum of the in vitro liver tissue includes the steps of illuminating an area of the in vitro liver tissue with a white light, and collecting diffused reflectance light returned from the illuminated area of the in vitro liver tissue.

In a preferable embodiment, the excitation light comprises a coherent light that has a wavelength between about 320 nm and about 340 nm. Accordingly, the first peak wavelength $\lambda_1$ of the fluorescence spectrum is in a range of about 370 nm to about 400 nm, and the second peak wavelength $\lambda_2$ of the fluorescence spectrum is in a range of about 460 nm to about 500 nm.

The method further includes the step of identifying the in vitro liver tissue as a normal liver tissue when the first peak wavelength $\lambda_1$ and the second peak wavelength $\lambda_2$ of the fluorescence spectrum are substantially at about 395 nm and about 470 nm, respectively, and a ratio of the corresponding first peak intensity $F(\lambda_1)$ to the corresponding second peak intensity $F(\lambda_2)$ of the fluorescence spectrum is less than one, and the intensity of the diffused reflectance spectrum is substantially unchanged over the predetermined wavelength region from about 600 nm to about 800 nm.

Moreover, the method includes the step of identifying the in vitro liver tissue as a malignant liver tissue with a cirrhotic liver tissue when the first peak wavelength $\lambda_1$, and the second peak wavelength $\lambda_2$ of the fluorescence spectrum are substantially at about 395 nm and about 490 nm, respectively, and a ratio of the corresponding first peak intensity $F(\lambda_1)$ to the corresponding second peak intensity $F(\lambda_2)$ of the fluorescence spectrum is less than one, and the intensity of the diffused reflectance spectrum is substantially monotonically decreased over the predetermined wavelength region from about 600 nm to about 800 nm.

Furthermore, the method includes the step of identifying the in vitro liver tissue as a malignant liver tissue with a colon metastasis liver tissue when the first peak wavelength $\lambda_1$, and the second peak wavelength $\lambda_2$ of the fluorescence spectrum are substantially at about 380 nm and about 480 nm, respectively, and a ratio of the corresponding first peak intensity $F(\lambda_1)$ to the corresponding second peak intensity $F(\lambda_2)$ of the fluorescence spectrum is about one or greater than one, and the intensity of the diffused reflectance spectrum is monotonically decreased over the predetermined wavelength region from about 600 nm to about 800 nm.

In yet a further aspect, the present invention relates to an apparatus for identifying an in vitro liver tissue of a living subject. In one embodiment, the apparatus has a first light source, a second light source, a fiber optical probe coupled with the first light source and the second light source, a detector coupled with the fiber optical probe, and a controller coupled with the detector.

The first light source is adapted for emitting an excitation light with a wavelength between about 320 nm and about 340 nm. The excitation light can be a coherent light or a non-coherent light as long as it has adequate wavelength and intensity so as to induce fluorescent emission from tissue. The second light source is adapted for emitting a white light. In one embodiment, the excitation light comprises a coherent light. The fiber optical probe is used to deliver the coherent light and the white light to an area of an in vitro liver tissue to be identified proximal to a working end of the fiber optical probe, respectively. The detector, such as a spectrometer, is employed to receive from the working-end of the fiber optical probe fluorescent light returned from the area of the in vitro liver tissue of the living subject in response to illumination by the coherent light and diffused reflectance light returned from the area of the in vitro liver tissue of the living subject in response to illumination by the white light, and to provide frequency spectra of the returned fluorescent light and the returned diffused reflectance light, respectively. The controller is programmed to determine a first peak and a second peak of the frequency spectrum of the returned fluorescent light, and a spectral profile of the frequency spectrum of the returned diffused reflectance light in a predetermined wavelength region, respectively, so as to identify the in vitro liver tissue. The first peak of the frequency spectrum of the returned fluorescent light includes a first peak wavelength, $\lambda_1$, and a corresponding first peak intensity, $F(\lambda_1)$, and the second peak of the frequency spectrum of the returned fluorescent light includes a second peak wavelength, $\lambda_2$, and a corresponding second peak intensity, $F(\lambda_2)$. The spectral profile of the frequency spectrum of the returned diffused reflectance light includes a spectral shape and intensity, and the predetermined wavelength region is from about 600 nm to about 800 nm. The controller, in one embodiment, is associated with a computer.

In an alternative aspect, the present invention relates to a method for detecting a malignant liver tissue of in vivo liver tissues, wherein the in vivo liver tissues have at least a first area and a second area, and at least one of the first area and the second area contains a malignant liver tissue. In one embodiment, the method includes the steps of acquiring a fluorescence spectrum of the in vivo liver tissues from the first area, acquiring a diffused reflectance spectrum of the in vivo liver tissues from the first area, and identifying a blood absorption signature in the fluorescence spectrum at a first wavelength about 540 nm, and at a second wavelength about 580 nm, and a spectral profile of the diffused reflectance spectrum in a predetermined wavelength region, respectively, where the blood absorption signature in the fluorescence spectrum is corresponding to a spectral valley, and the spectral profile of the diffused reflectance spectrum includes a spectral shape and intensity, and the predetermined wavelength region is from about 600 nm to about 700 nm. The method further includes the step of repeating the above steps in the second area of the in vivo liver tissues.

Moreover, the method includes the step of identifying the in vivo liver tissue as a malignant liver tissue in one of the first area and the second area, wherein in the area no blood absorption signature is identified in the fluorescence spectrum at about 540 nm and about 580 nm, respectively, and the intensity of the diffused reflectance spectrum is substantially monotonically decreased over the predetermined wavelength region from about 600 nm to about 700 nm. The malignant liver tissue is further identified to have a primary liver tumor when the intensity of the fluorescence spectrum is at least three times larger than the intensity of the fluorescence spectrum from a normal liver tissue over a wavelength range of about 400 nm to about 600 nm, or a secondary liver tumor when the fluorescence spectrum has a first peak at a first peak wavelength about 400 nm and a second peak at a second peak wavelength about 480 nm, respectively, and a ratio of a corresponding first peak intensity to a corresponding second peak intensity to be substantially about one.

Additionally, the method includes the step of identifying the in vivo liver tissue as a normal liver tissue in one of the first area and the second area, wherein in the area the blood absorption signature is identified in the fluorescence spectrum at about 540 nm and about 580 nm, respectively, and the intensity of the diffused reflectance spectrum is substantially unchanged over the predetermined wavelength region from about 600 nm to about 700 nm.

In one aspect, the present invention relates to an apparatus for detecting a malignant liver tissue of in vivo liver tissues, wherein the in vivo liver tissues have at least a first area and a second area, and at least one of the first area and the second area contains a malignant liver tissue. In one embodiment, the apparatus includes a first light source adapted for emitting an excitation light, and a second light source adapted for emitting a white light. The excitation light can be a coherent light or a non-coherent light as long as it has adequate wavelength and intensity so as to induce fluorescent emission from tissue. In one embodiment, the first light source has a laser, preferably, emitting a coherent light with a wavelength between about 320 nm and about 340 nm. The second light source has a halogen light source.

Furthermore, the apparatus includes a fiber optical probe that is coupled with the first light source and the second light source so as to deliver the coherent light and the white light to an area of an in vivo liver tissues to be identified proximal to a working end of the fiber optical probe, respectively. Moreover, the apparatus includes a detector coupled with the fiber optical probe so as to receive from the working end of the fiber optical probe fluorescent light returned from the area of the in vivo liver tissues of the living subject in response to illumination by the coherent light and diffused reflectance light returned from the area of the in vivo liver tissues of the living subject in response to illumination by the white light, and to provide frequency spectra of the returned fluorescent light and the returned diffused reflectance light, respectively. Additionally, the apparatus includes a controller coupled with the detector and programmed to determine a blood absorption signature in the frequency spectrum of the returned fluorescent light at a first wavelength about 540 nm, and at a second wavelength about 580 nm, and a spectral profile of the frequency spectrum of the returned diffused reflectance light in a predetermined wavelength region, respectively, wherein the blood absorption signature in the frequency spectrum of the returned fluorescent light is corresponding to a spectral valley, and wherein the spectral profile of the frequency spectrum of the returned diffused reflectance light includes a spectral shape and intensity, and the predetermined wavelength region is from about 600 nm to about 700 nm.

In another aspect, the present invention relates to a method for identifying an in vitro tissue of an organ of a living subject. In one embodiment, the method has the steps of acquiring a fluorescence spectrum of an in vitro tissue to be identified, acquiring a diffused reflectance spectrum of the in vitro tissue, and identifying a first peak and a second peak of the fluorescence spectrum, and a spectral profile of the diffused reflectance spectrum in a predetermined wavelength region, respectively, so as to identify the in vitro tissue, wherein the first peak of the fluorescence spectrum includes a first peak wavelength, $\lambda_1$, and a corresponding first peak intensity, $F(\lambda_1)$, and the second peak of the fluorescence spectrum includes a second peak wavelength, $\lambda_2$, and a corresponding second peak intensity, $F(\lambda_2)$, and wherein the spectral profile of the diffused reflectance spectrum includes a spectral shape and intensity.

In yet another aspect, the present invention relates to a method of optimal placement of a radio frequency probe for a radio frequency ablation of a liver tumor in liver tissues of a living subject, wherein the radio frequency probe has a plurality of electrodes, each electrode adapted for transmitting a radio frequency energy applied to an area of the liver tissues in which a working end of the electrode is located, and a plurality of optical fibers adapted such that when the radio frequency probe is placed into the liver tissues, each optical fiber is adapted for an optical spectrum measurement in an area of the liver tissues in which a working end of the optical fiber is located. In one embodiment, the method comprises the steps of (a) placing the radio frequency probe into the liver tissues at an initially selected position, (b) acquiring optical spectra from each area of the liver tissues in which a working end of the plurality of optical fibers is located, respectively, (c) identifying a type of the liver tissues in each area from the acquired optical spectra corresponding to the area, respectively, (d) adjusting the position of the radio frequency probe from the initially selected position so as to find a new position if a normal liver tissue is identified in at least one area in which a working end of the plurality of optical fibers is located, (e) repealing steps (b)-(d) until no normal liver tissue is identified in any area in which a working end of the plurality of optical fibers is located in a current position of the radio frequency probe, and (f) choosing the current position as an optimal position of the radio frequency probe for a radio frequency ablation of a liver tumor in liver tissues.

In a further aspect, the present invention relates to an apparatus of optimal placement of a radio frequency probe for a radio frequency ablation of a liver tumor in liver tissues of a living subject. In one embodiment, the apparatus includes a first light source adapted for emitting a coherent light, and a second light source adapted for emitting a white light. The apparatus further includes a radio frequency probe coupled with the first light source and the second light source and placed at an initially selected position in the liver tissues, wherein the radio frequency probe have a plurality of electrodes, each electrode adapted for transmitting a radio frequency energy applied to an area of the liver tumor in which a working end of the electrode is located, and a plurality of optical fibers is adapted such that when the radio frequency probe is placed into the liver tissues, each optical fiber is adapted for an optical spectrum measurement in an area of the predetermined margin in which a working end of the optical fiber is located. Moreover, the apparatus includes a detector coupled with the radio frequency probe so as to acquire optical spectra from each area of the liver tissues in which a working end of the plurality of optical fibers is located, respectively. Additionally, the apparatus includes a controller coupled with the detector and programmed to identify a liver tissue type in each area of the liver tissues from the acquired optical spectra corresponding to each area, respectively, so as to determine if the placement of the radio frequency probe in the initially selected position is optimal. The apparatus further include a radio frequency energy source coupled with the radio frequency probe for providing the radio frequency energy.

In yet a further aspect, the present invention relates to a method for controlling a volume of a radio frequency ablation of a liver tumor in liver tissues of a living subject intra-operatively. In one embodiment, the method includes the step of placing a radio frequency probe into a volumetric center of a liver tumor to be ablated. The radio frequency probe has a plurality of electrodes, where each electrode adapted for transmitting a radio frequency energy applied to an area of the liver tumor in which a working end of the electrode is located. The radio frequency probe further has a plurality of optical fibers adapted such that when the radio frequency probe is placed into the volumetic center of the liver tumor, working ends of the plurality of optical fibers are positioned at a predetermined margin of the liver tumor, where each optical fiber adapted for an optical spectrum measurement in an area of the predetermined margin in which a working end of the optical fiber is located.

Furthermore, the method includes the steps of conducting a radio frequency ablation of the liver tumor with the radio frequency probe, acquiring optical spectra from each area of the predetermined margin of the liver tumor in which a working end of the plurality of optical fibers is located, monitoring liver tissue coagulation in each area of the predetermined margin from the acquired optical spectra corresponding to each area, and terminating the radio frequency ablation when the liver tissue coagulation in the predetermined margin appears in all monitored areas. The optical spectra include a fluorescence spectrum and a diffused reflectance spectrum.

In an alternative aspect, the present invention relates to an apparatus for monitoring a volume of a radio frequency ablation of a liver tumor in liver tissues of a living subject intra-operatively. In one embodiment, the apparatus comprises at least one light source that is adapted for emitting a light. The at least one light source, in one embodiment, has a coherent light source, and in another embodiment, has a white light source. Furthermore, the apparatus has a radio frequency energy source adapted for providing a radio frequency energy. Moreover, the apparatus has a radio frequency probe that is coupled with the radio frequency energy source and the at least one light source and placed at a volumetric center of a liver tumor to be ablated. The radio frequency probe has a plurality of electrodes, where each electrode is adapted for transmitting a radio frequency energy applied to an area of the liver tumor in which a working end of the electrode is located. The radio frequency probe further has a plurality of optical fibers adapted such that when the radio frequency probe is placed into the volumetic center of the liver tumor, working ends of the plurality of optical fibers are positioned at a predetermined margin of the liver tumor, where each optical fiber is adapted for an optical spectrum measurement in an area of the predetermined margin in which a working end of the optical fiber is located. Additionally, the apparatus has a detector coupled with the radio frequency probe so as to acquire optical spectra from each area of the predetermined margin of the liver tumor in which a working end of the plurality of optical fibers is located. Furthermore, the apparatus has a controller coupled with the detector and programmed to intra-operatively monitor liver tissue coagulation in each area of the predetermined margin from the acquired optical spectra corresponding to each area.

In another aspect, the present invention relates to a probe for ablation of a tumor in tissues of a living subject. In one embodiment, the probe comprises a plurality of first electrodes, each electrode adapted for transmitting a radio frequency energy to an area of the tissues where a working end of a corresponding first electrode is located, and at least one second electrode adapted for acquiring an optical spectrum measurement in an area of the tissues where a working end of the second electrode is located. In one embodiment, the working ends of the plurality of first electrodes are at staggered length aligned to be implanted in the tissues, and the second electrode comprises a working end, and an optical fiber connected to the working end.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
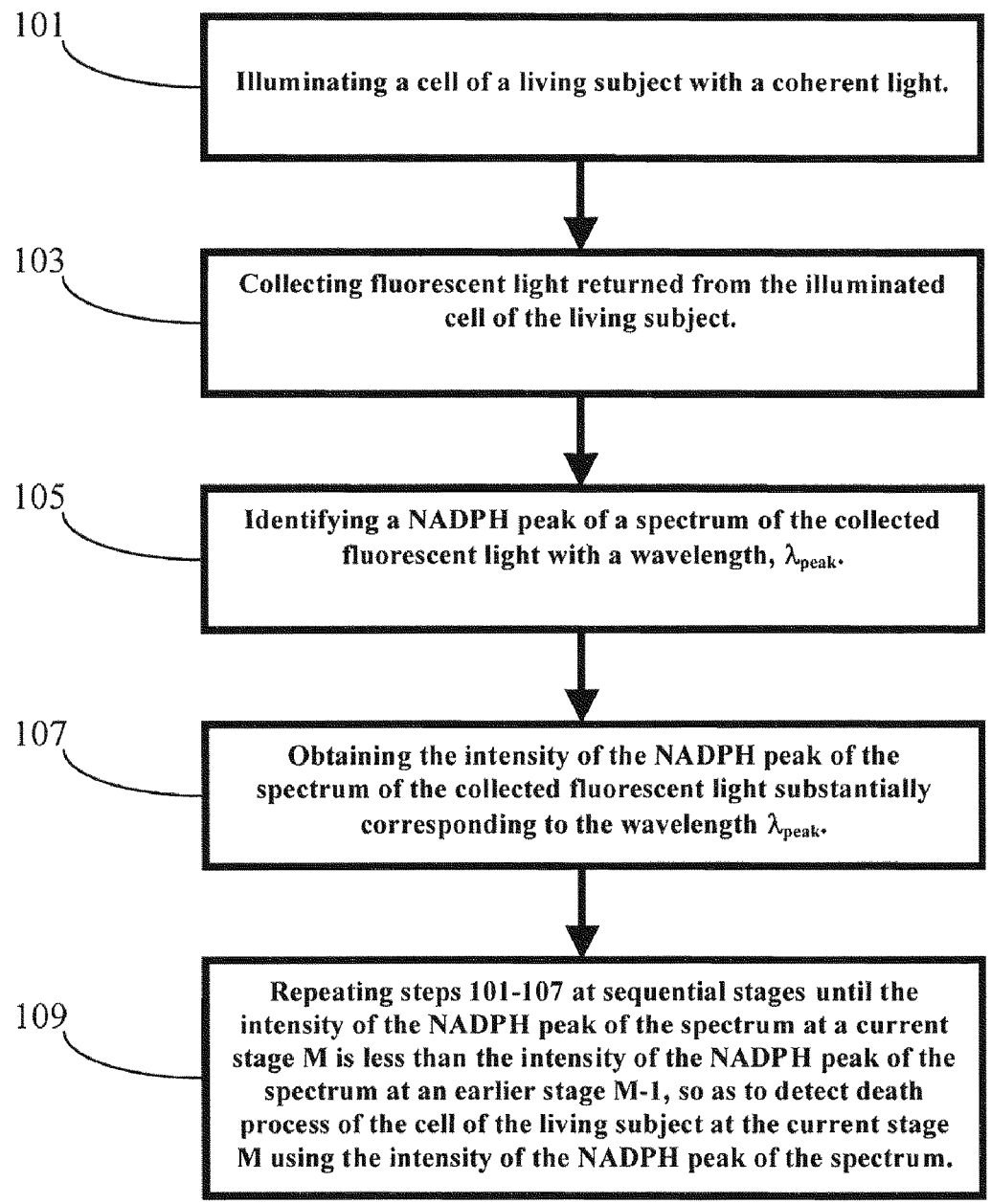
FIG. 1 is a flowchart for detecting death process of a cell and/or tissue of a living subject according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing various embodiments of the invention and how to practice the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab-testing monkey.

As used herein, "position," "place," and "locate" are synonyms in the specification.

Overview of the Invention

This invention in one aspect relates to a method for detecting death process of the cell or tissue of the living subject. The living subject is either a human or an animal. The cell or tissue of the living subject may have been subject to neurodegenerative disease, hyperthermia, cisplatin and/or chemotherapy for various periods of time. Among other things, one unique feature of the present invention is the utilization of a NAD(P)H fluorescence-signal for diagnosing apoptosis of a cell or tissue of a living subject in an early stage and detecting death process of the cell or tissue of the living subject correspondingly.

Referring in general to FIG. 1, the method for detecting death process of a cell or tissue of the living subject according to one embodiment of the present invention is schematically illustrated in a flow chart. In one embodiment, at step 101, the cell of the living subject is illuminated with a coherent light at an incident wavelength that is between 330 nm and 400 nm. In one example, the incident coherent light is emitted from a laser light source with a wavelength substantially at around 337 nm. At step 103, fluorescent light returned from the illuminated cell of the living subject is collected to form a frequency spectrum or spectra. For instance, a portable, optical spectroscopic system can be employed to acquire the fluorescence spectra. At step 105, a NAD(P)H peak of the collected fluorescent spectra with a wavelength, $\lambda_{peak}$, is identified. At step 107, the intensity of the NAD(P)H peak of the collected fluorescent spectra corresponding to the wavelength speak is obtained, where the wavelength $\lambda_{peak}$ is substantially at around 460 nm. At step 109, steps 101-107 are repeated at sequential stages until the intensity of the NAD(P)H peak of the spectrum at a current stage M is less than the intensity of the NAD(P)H peak of the spectrum at an earlier stage M−1, so as to detect death process of the cell of the living subject at the current stage M using the intensity or the NAD(P)H peak of the spectrum. The stage M−1 is immediately prior to the current stage M, M being an integer greater than 1. Same process can be applied to cells, tissue or tissues of a living subject.

The cell or tissue of the living subject experiences apoptosis leading to death at the current stage M when the NAD(P)H peak intensity at the current stage M is less than the NAD(P)H peak intensity at the earlier stage M−1. In one embodiment, the cell or tissue of the living subject is native at a first stage and is subject to hyperthermia and/or cisplatin for various periods of time at the sequential stages.

In another aspect, the present invention relates to a method for identifying and detecting tissue types of liver tissues of a living subject by using unique spectral signatures of the liver tissues in optical spectroscopy. The method in general includes the steps of acquiring a fluorescence spectrum of a liver tissue to be identified, acquiring a diffused reflectance spectrum of the liver tissue, and determining spectral signatures associated with the liver tissue in the acquired fluorescence and diffused reflectance spectra so as to identify the tissue type of the liver tissue. The step of acquiring the fluorescence spectrum of the liver tissue includes the steps of illuminating an area of the liver tissue with an excitation light, and collecting fluorescent light returned from the illuminated area of the liver tissue. The excitation light can be a coherent light or a non-coherent light as long as it has adequate wavelength and intensity so as to induce fluorescent emission from tissue. The step of acquiring the diffused reflectance spectrum of the liver tissue includes the steps of illuminating an area of the liver tissue with a white light, and collecting diffused reflectance light returned from the illuminated area of the liver tissue. The fluorescence spectrum and the diffused reflectance spectrum can be acquired from the liver tissue in either order.

Because of the differences in structure and morphology at the cellular and sub-cellular level in different types of tissues, optical properties of the different types of tissues, in terms of spectral signatures in fluorescence and diffused reflectance spectra, vary accordingly. These variations in optical spectroscopy for different tissues are used for detecting tissue abnormalities and identifying the tissue type according to the embodiments of the present invention. For example, for excitation of a coherent light having a wavelength between about 320 nm and about 340 nm, the fluorescence spectrum from an in vitro normal liver tissue has a first peak and a second peak with a wavelength about 395 nm and about 470 nm, respectively, and a ratio of the corresponding first peak intensity to the corresponding second peak intensity of the fluorescence spectrum being much less than one. The fluorescence spectrum from an in vitro malignant liver tissue with a cirrhotic liver tissue has a first peak and a second peak with a wavelength about 395 nm and about 490 nm, respectively, and a ratio of the corresponding first peak intensity to the corresponding second peak intensity of the fluorescence spectrum being much less than one. And the fluorescence spectrum from an in vitro malignant liver tissue with a cirrhotic liver tissue has a first peak and a second peak with a wavelength about 380 nm and about 480 nm, respectively, and a ratio of the corresponding first peak intensity to the corresponding second peak intensity of the fluorescence spectrum being substantially about one. For illumination of a white light, the diffused reflectance spectrum from the normal liver tissue is substantially unchanged over the predetermined wavelength region from about 600 nm to about 800 nm. While the diffused reflectance spectrum from the normal liver tissue is monotonically decreased over the predetermined wavelength region from about 600 nm to about 800 nm.

For in vivo liver tissues, a blood absorption signature in the fluorescence spectrum at a first wavelength about 540 nm, and at a second wavelength about 580 nm appears only for a normal liver tissue, and the diffused reflectance spectrum is substantially unchanged over the predetermined wavelength region from about 600 nm to about 700 nm for a normal liver tissue. However, for a malignant liver tissue, the diffused reflectance spectrum is monotonically decreased over the predetermined wavelength region from about 600 nm to about 800 nm.

Furthermore, the present invention discloses a method of optimal placement of a radio frequency probe for a RFA of a liver tumor in liver tissues of a living subject. The method is mainly based on precisely identifying the type of the liver tissues proximal to the working end of the radio frequency probe using fluorescence and diffused reflectance spectra. The fluorescence and diffused reflectance spectra of the liver tissues are monitored and acquired through the radio frequency probe. While liver is chosen as an example herein, the present invention can be practiced with respect to other organs of a living subject.

Figure 11:
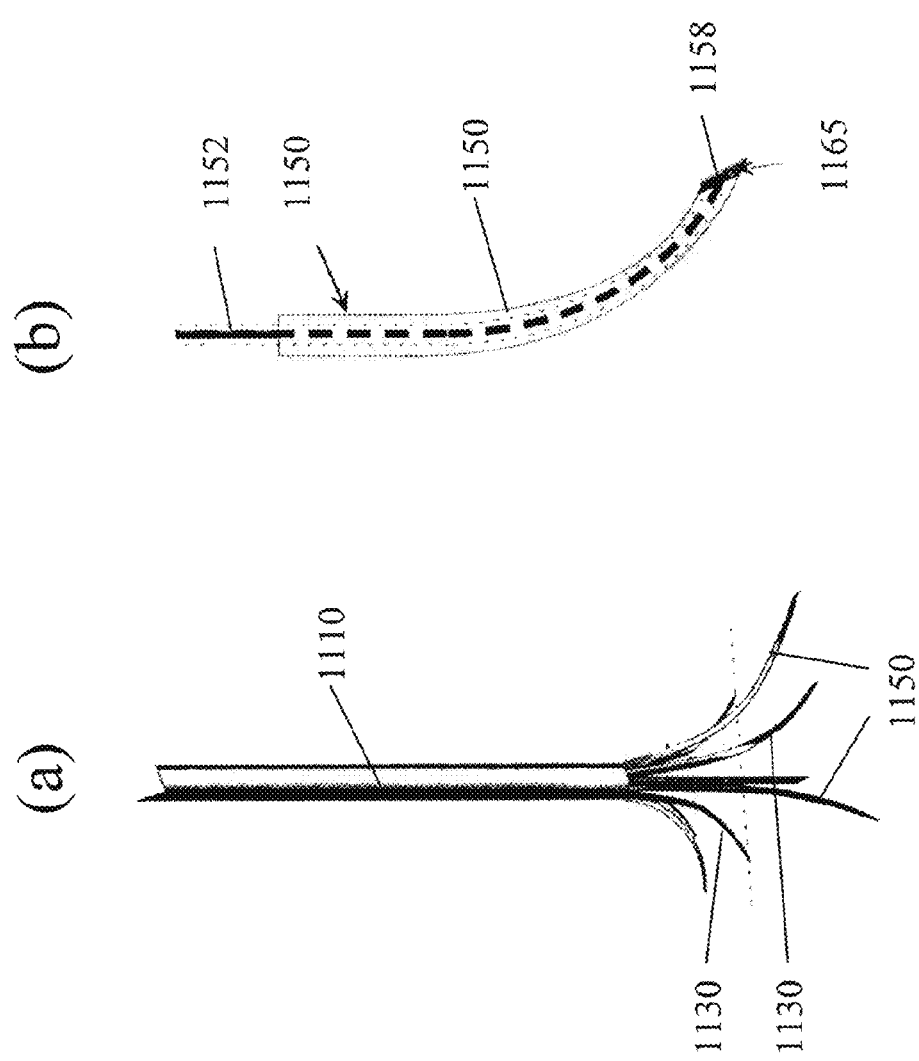
FIG. 11 shows schematically a radio frequency probe according to one embodiment of the present invention: (a) a perspective view of the radio frequency probe, and (b) a cross-section view of an electrode of the radio frequency probe having an optical fiber.

Referring now to FIG. 11, a radio frequency probe 1110 for a radio frequency ablation of a tumor in tissues of a living subject is shown according to one embodiment of the present invention. The radio frequency probe 1110 has a plurality of first electrodes 1130. Each of the plurality of first electrodes 1130 is adapted for transmitting a radio frequency energy to an area of the liver tissues where a working end of the corresponding first electrode is located. The radio frequency probe 1110 further has a plurality of second electrodes 1150. Each of a plurality of second electrodes 1150 is adapted for acquiring an optical spectrum measurement in an area of the tissues where a working end of the corresponding second electrode 1150 is located. As shown in FIG. 11b, a second electrode 1150 includes a tubular body 1154 sufficiently rigid to penetrate the liver tissue without significant deflection, a working end 1156, and an optical fiber 1152 passed through the hollow interior of the tubular body 1154 to a window 1158 at the working end 1156 of the second electrode 1150. Each of the plurality of second electrodes 1150 can be individually positioned to take a series of optical spectrum measurements so as to identify the tissue in the area of the liver tissues where the working end of the corresponding second electrode 1150 is located. Moreover, the first electrodes and the second electrodes each can have working ends with same or different lengths. In one embodiment, the working ends of the first and/or second electrodes are at staggered length aligned to be implanted in the tissues for optimal result(s).

Figure 12:
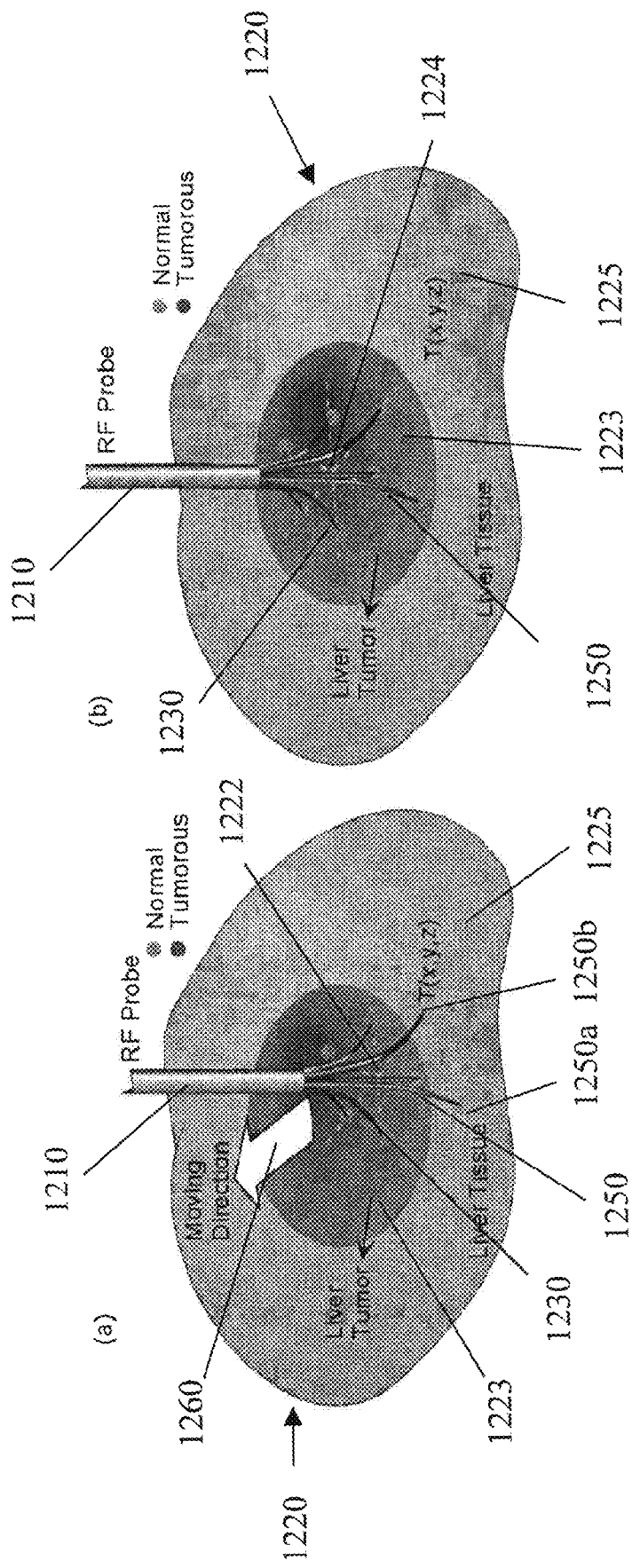
FIG. 12 shows schematically optimal placement of a radio frequency probe in liver tissues according to one embodiment of the present invention: (a) a perspective view of the radio frequency probe placed in an non-optimized position, and (b) a perspective view of the radio frequency probe in an optimized position.

Specifically, the disclosed method of optimal placement of the radio frequency probe for the RFA comprises the following steps: at step (a), the radio frequency probe is placed into the liver tissues at an initially selected position. At step (b), optical spectra, such as fluorescence and diffused reflectance spectra, are acquired from each area of the liver tissues in which a working end of the plurality of second electrodes (optical fibers) is located. At step (c), a type of the liver tissues is identified in each area from the fluorescence and diffused reflectance spectra corresponding to the area. At step (d), the position of the radio frequency probe is adjusted from the initially selected position so as to find a new position if a normal liver tissue is identified in at least one area in which a working end of the plurality of second electrodes is located. Referring to FIG. 12a, a radio frequency probe 1210 is placed into liver tissues 1220 at an initially selected position 1222. The liver tissues 1220 have a liver tumor 1223 and a normal liver tissue 1225 surrounding the liver tumor 1223. As shown in FIG. 12a, the radio frequency probe 1210 in the initially selected position 1222 has two second electrodes 1250 located in areas 1225a and 1225b of the normal liver tissue 1225, respectively. Correspondingly, normal liver tissues in areas 1225a and 1225b will be identified by fluorescence and diffused reflectance spectra corresponding to areas 1225a and 1225b, respectively. In other words, the initially selected position 1222 of the radio frequency probe 1210 is not optimal. The position of the radio frequency probe 1210 needs to be adjusted, for example, along direction 1260 or other direction(s). These procedures, steps (a)-(d), are repeated until no normal liver tissue is identified in any area in which a working end of the plurality of second electrodes is located in a current position of the radio frequency probe. As shown in FIG. 12b, the radio frequency probe 1210 is positioned at a current position 1224 such that all of the plurality of second electrodes 1250 and the plurality of first electrodes 1230 are placed inside the liver tumor 1223, and thus, in the current position 1224 of the radio frequency probe 1210, no normal liver tissue is identified in any area where a working end of the plurality of second electrodes 1250 is located. The current position 1224 is then chosen as an optimal position of the radio frequency probe 1210 for a radio frequency ablation of the liver tumor 1223 in liver tissues 1220.

Figure 13:
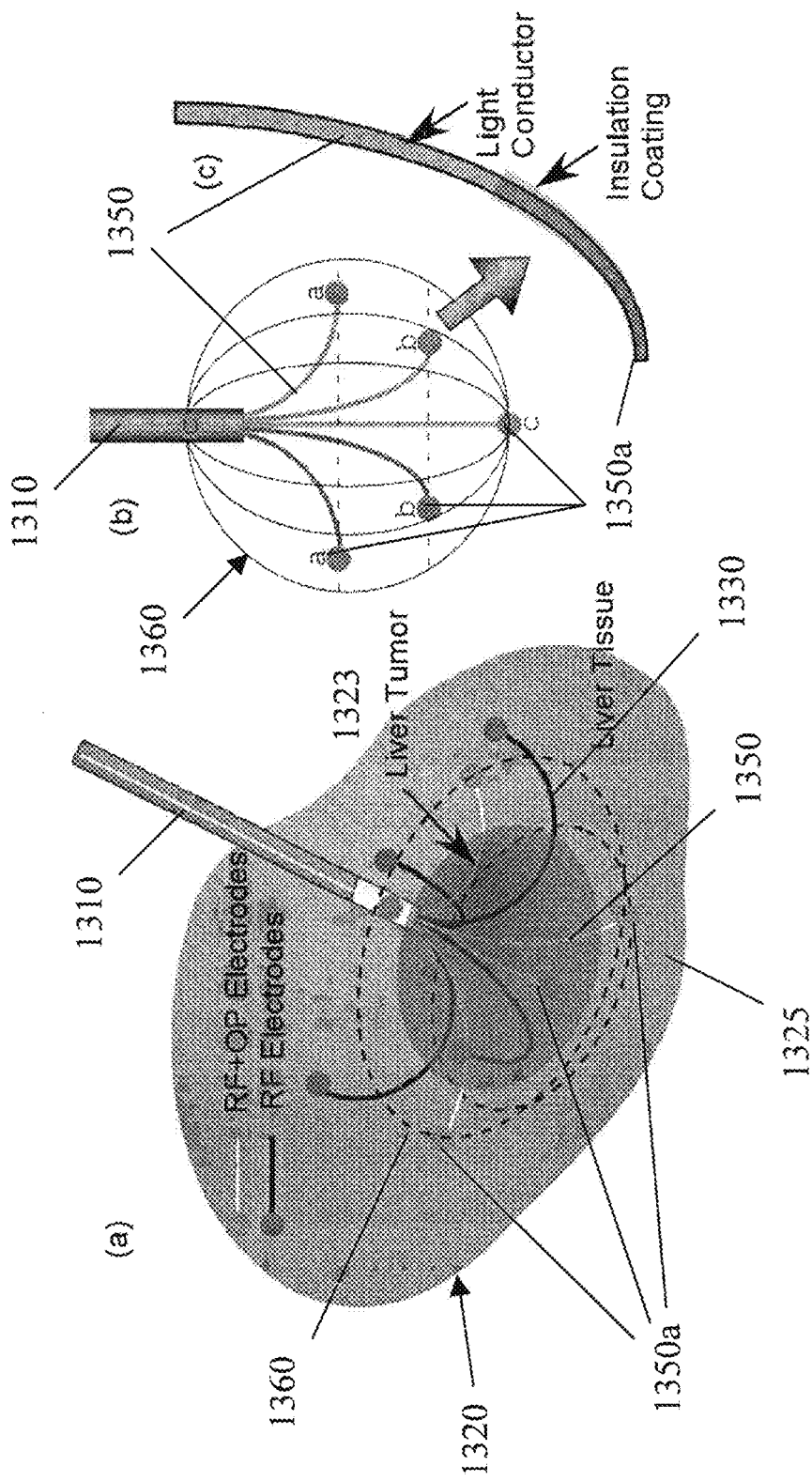
FIG. 13 shows schematically a radio frequency probe in monitoring a volume of a radio frequency ablation lesion according to one embodiment of the present invention: (a) a perspective view of the radio frequency probe placed in a volumetric center of a liver tumor to be ablated, (b) a side view of the radio frequency probe placed in the volumetric center of the liver tumor, and (c) a structure of a radio frequency ablation electrode with optical feedback function.

The present invention also discloses a method for monitoring and controlling a volume of a radio frequency ablation of a liver tumor in liver tissues of a living subject intra-operatively by utilizing optical properties of coagulation in the liver tissues. As shown in FIG. 13, a radio frequency probe 1310 is placed in a volumetric center of a liver tumor 1323 to be ablated, such that the working ends 1350a of the plurality of second electrodes (optical fibers) 1350 of the radio frequency probe 1310 are positioned at a predetermined margin 1360 of the liver tumor 1323. Each optical fiber 1350 is adapted for an optical spectrum measurement in an area of the predetermined margin 1360 where a working end 1350a of the optical fiber 1350 is located. The predetermined margin 1360 of the liver tumor 1323 is a desired coagulation boundary, for example, 1 cm beyond the tumor margin. During the course of the radio frequency ablation of the liver tumor 1323 with the radio frequency probe 1310, optical spectra are continuously acquired from each area of the predetermined margin 1360 of the liver tumor 1323 where a working end 1350a of the plurality of optical fibers 1350 is located, so that liver tissue coagulation in each area 1350a of the predetermined margin 1360 is monitored in real time from the optical spectra corresponding to the area. The radio frequency ablation will be terminated when the liver tissue coagulation in the predetermined margin appears in all monitored areas.

Figure 2:
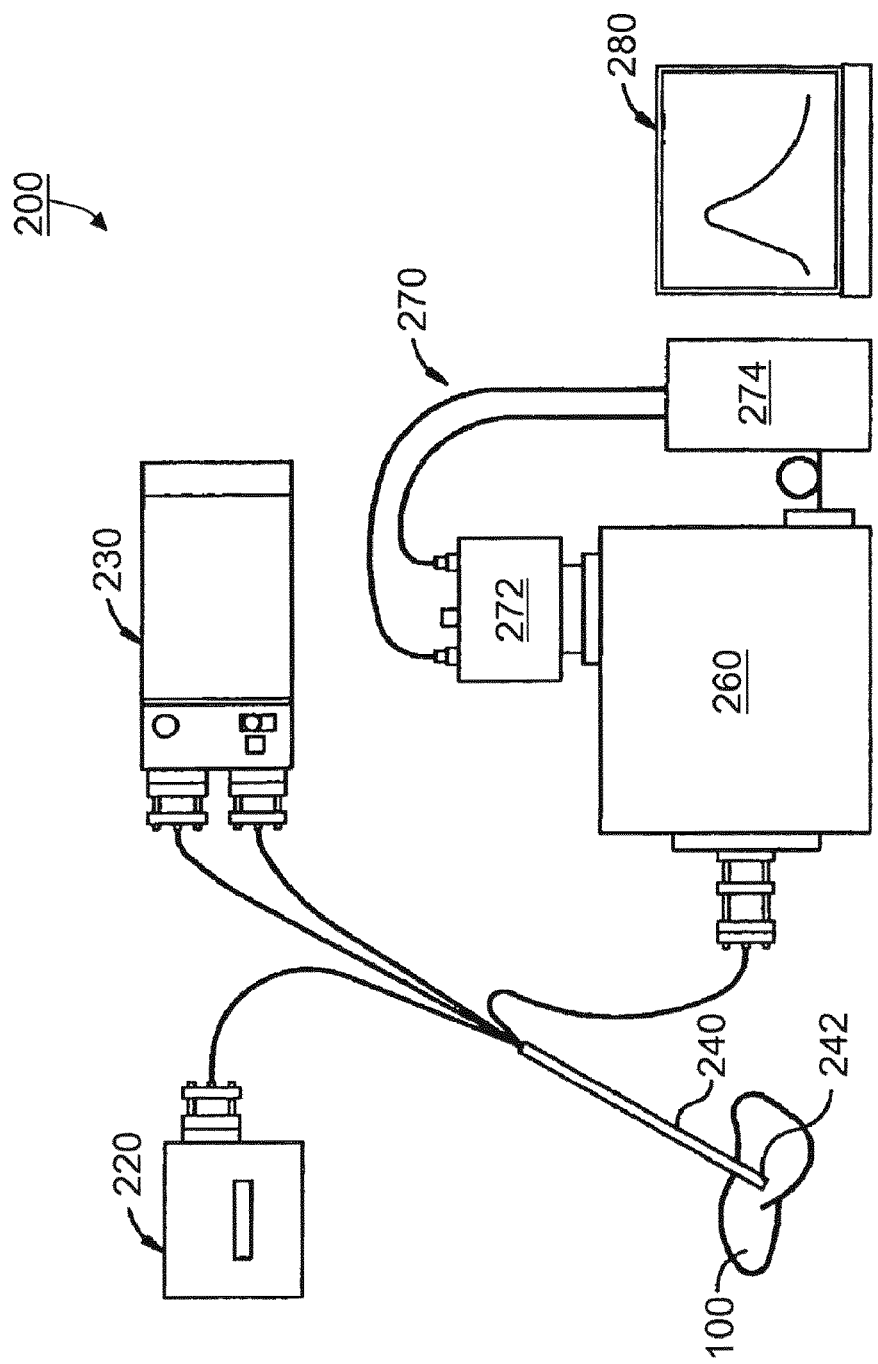
FIG. 2 shows schematically an apparatus according to one embodiment of the present invention.

Referring now to FIG. 2, in one embodiment of the present invention, an apparatus 200 includes a source of white light 220 and a source of laser light 230, a fiber optical probe 240 coupled with the source of white light 220 and the source of laser light 230 so as to deliver the white light and the laser light to a working end 242 of the fiber optical probe 240, respectively, and a spectrograph or spectroscope 260 coupled with the fiber optical probe 240 so as to respectively receive diffused reflectance light returned from and fluorescent light emitted from a cell or tissue of a living subject 100 that is contacted by the working end 242 of the fiber optical probe 240. The spectrograph 260 also provides a frequency spectrum of the received fluorescent light. The apparatus 200 further has a frequency amplitude detector 270 in the form of a Charge-Coupled Device (hereinafter "CCD") camera 272 with a camera controller 274. Moreover, the apparatus 200 includes a processor 280 in the form of a computer, such as a personal computer (hereinafter "PC"), coupled with the spectrograph 260 through the detector 270. The processor 280 is adapted for analyzing the frequency spectrum of light carried from the working end 242 of the probe 240 to the spectrometer 260.

The processor 280 can be programmed for different purposes as part of the present invention. For example, for detecting cell or tissue death process, the processor 280 is programmed to identify a NAD(P)H peak of the frequency spectrum of the returned fluorescent light with a wavelength $\lambda_{peak}$ and the corresponding intensity of the NAD(P)H peak of the spectrum of the returned fluorescent light. For identifying a tissue type of an in vitro liver tissue of a living subject, the processor 280 is programmed to determine a first peak and a second peak of the frequency spectrum of the returned fluorescent light, and a spectral profile of the frequency spectrum of the returned diffused reflectance light in a predetermined wavelength region from about 600 nm to about 800 nm, respectively. For detecting a malignant tissue of in vivo liver tissues of a living subject, the processor 280 is programmed to determine a blood absorption signature in the frequency spectrum of the returned fluorescent light at a first wavelength about 540 nm, and at a second wavelength about 580 nm, and a spectral profile of the frequency spectrum of the returned diffused reflectance light in a predetermined wavelength region from about 600 nm to about 700 nm, respectively.

Several types of laser light sources can be used to practice the present invention. In one embodiment, for example, a 337 nm high-pressure nitrogen laser 230, e.g., a high pressure nitrogen dye laser from Oriel Corporation, Stratford, Conn., is used as an excitation source for fluorescence measurements. A halogen light source (Fiber Lite, Model 180, Edmund Industrial Optics, Barrington, N.J.) emitting broadband white light from about 400 nm to 850 nm is used as the excitation light sources for diffused reflectance spectroscopy. Light delivery and collection can be achieved with a proper fiber optical probe such as a Gaser fiber optical probe 240 (Visionex, Inc., Atlanta, Ga.). This probe comprises a plurality of individual wave guides in the form of 300 micron core diameter glass fibers, wherein two of the plurality of individual wave guides are employed to deliver white light and laser pulses to the detecting region of the organisms through the working end 242 of the probe 240, respectively, while the remaining wave guides are used to collect diffused reflectance light returned from and fluorescence emission induced by the incident laser light through the working end 242 of the probe 240, respectively. Prior to the measurement, the probe 240 is gas-sterilized, or low temperature plasma-sterilized, and then set up the operating field. The detailed structure and operation of the probe are exemplified in U.S. Pat. No. 6,377, 841, which is incorporated herein by reference.

The collected diffused reflectance light and fluorescent light are carried by the fiber optical probe 240, respectively, to the spectrograph 260, e.g., a Triax 180 from Instruments S.A., Inc., Edison, N.J., where it is dispersed and detected with detector 270, which is in the form of a CCD camera 272 with a camera controller 274, and projected onto a sensor array of a thermoelectrically cooled CCD camera 272, e.g., a Spectra One from Instruments S.A., Inc. For fluorescence measurements, reflected laser light was eliminated with two 360 nm long pass filters placed in front of entrance slit of the spectrograph 260. In one embodiment, a medical-grade isolation transformer (IT1500-4, Dale Technology Corporation, New York) is used with the portable spectroscopic system to comply with the electrical safety standard of the operating room.

The wavelength dependent light intensity recorded by the CCD camera 272 is then read, stored and analyzed (and may be displayed) by the processor 280. The recorded spectral data can be analyzed according to a specific method or procedure as part of the present invention. In this procedure, the recorded optical spectra are processed to eliminate the artifacts in them, that is, baseline is first removed from the spectra, and calibration factors derived from a standard calibration procedure are then multiplied to the spectra to remove wavelength-dependent characteristics of the spectroscopic system 200. The processed spectra are then analyzed to identify spectral variations in line-shape and intensity induced by the apoptosis of the cell or tissue of the living subject, and/or by liver tumors.

These and other aspects of the present invention are further described in the following section. Without intend to limit the scope of the invention, further exemplary procedures and preliminary experimental results of the same according to the embodiments of the present invention are given below.

ADDITIONAL METHODS, IMPLEMENTATIONS AND EXAMPLES OF THE INVENTION

Example 1

Cell and/or Tissue Death Process Detection

In one embodiment of the present invention, a cell or tissue of a living subject was native at a first stage and was subject to hyperthermia and/or cisplatin for various periods of time at the sequential stages. The cells or tissues of the living subject to be diagnosed were human colon adenocarcinoma cells (SW480). The NAD(P)H peak of the spectrum of the returned fluorescent light from the cell or tissue of the living subject, which was illuminated by the coherent light with an incident wavelength around 337 nm, was substantially at a wavelength around 460 nm. The NAD(P)H peak wavelength $\lambda_{peak}$ did not shifted from 460 nm for the cell or tissue of the living subject at different stages. However, the corresponding intensity of the NAD(P)H peak of the returned fluorescent spectrum dropped dramatically when the cell or tissue of the living subject were subject to hyperthermia and/or cisplatin for various periods of time at the sequential stages. It is one of the disclosures of the present invention that the cell or tissue of the living subject experiences apoptosis leading to death at the current stage when the NAD(P)H peak intensity at the current stage was less than the NAD(P)H peak intensity at an earlier stage immediately prior to the current stage.

Figure 3:
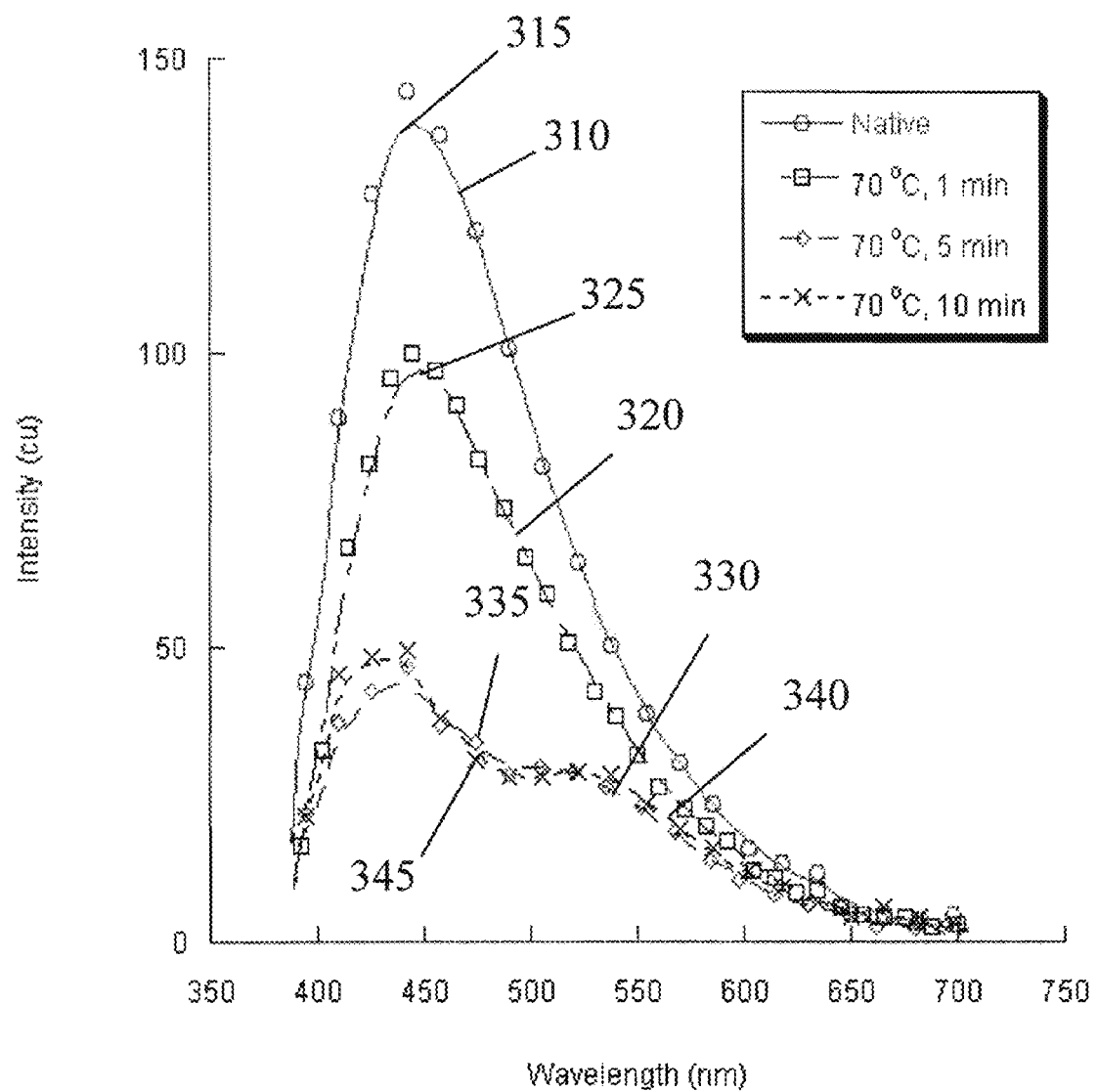
FIG. 3 shows fluorescence spectra from human colon adenocarcinoma cells (SW480) heated at 70° C. for 1 minute, 5 minutes and 10 minutes, respectively.
Figure 4:
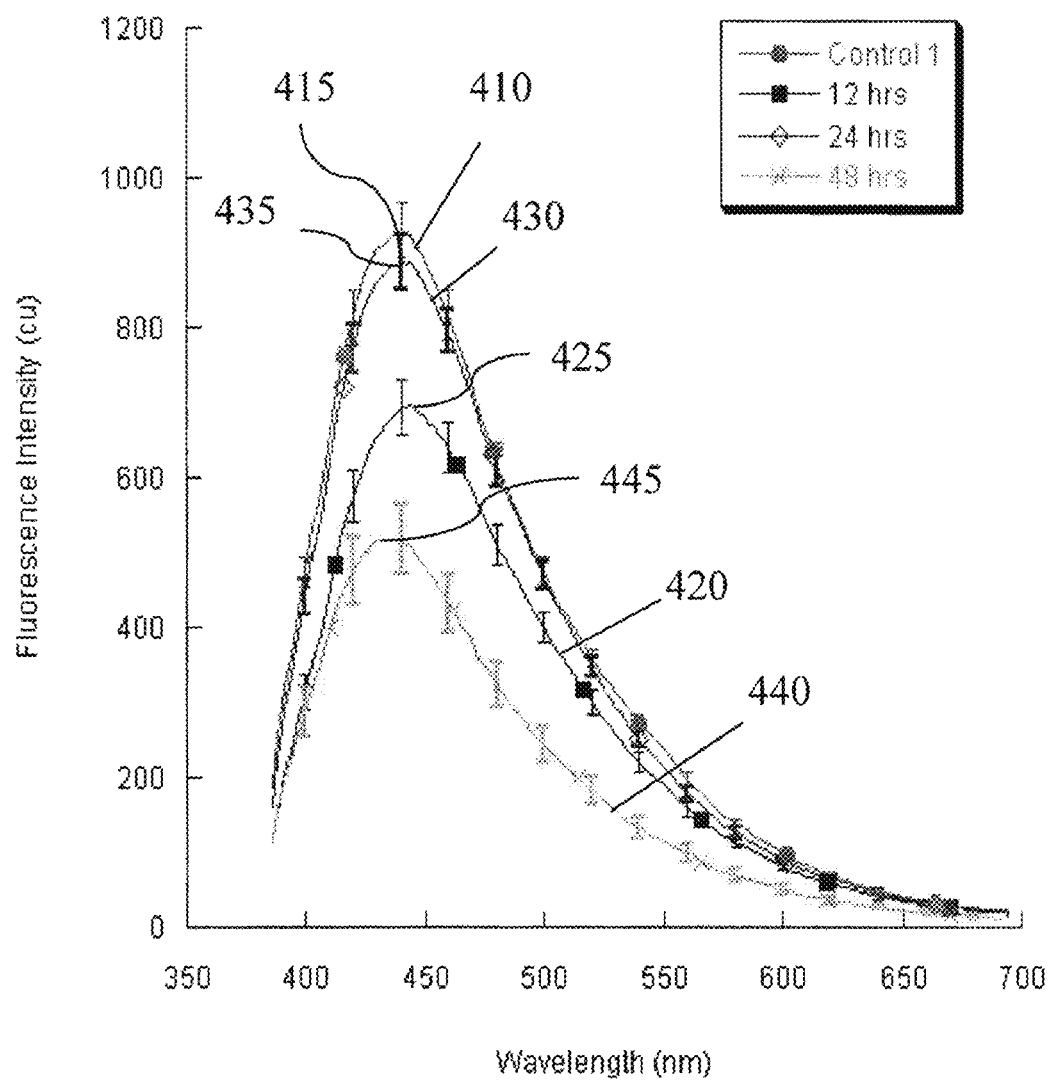
FIG. 4 shows fluorescence spectra from human colon adenocarcinoma cells (SW480) at different stages of apoptotic death.

Referring now to FIGS. 3 and 4, and first to FIG. 3, the fluorescent spectra emitted from the colon adenocarcinoma cells that were excited by the coherent light with an incident wavelength around 337 nm and treated with mild hyperthermia at 70° C. for various periods of time at sequential stages were shown. More specifically, spectrum curve 310 was from the cells at a first stage that were native, spectrum curves 320 was from the cells at a subsequent second stage which were treated for 1 minute, spectrum curves 330 was from the cells at a subsequent third stage that were treated for 5 minute, and spectrum curves 340 was from the cells at a subsequent fourth stage which were treated for 10 minute.

As shown in FIG. 3, all four fluorescence spectrum curves 310, 320, 330 and 340 have identifiable peaks of the fluorescence intensity at a wavelength around 460 nm, which were indicated by 315, 325, 335 and 345, respectively. The fluorescent peaks 315, 325, 335 and 345 at wavelength 460 nm were respectively identified as a NAD(P)H signal for the cells at the corresponding stages. Interestingly, a unique feature was shown in FIG. 3, where the intensity of the NAD(P)H peak of the spectrum decreases as the cells were treated with mild hyperthermia at 70° C. for various periods of time at sequential stages. For example, for the cells at the first stage that were native, the intensity of the NAD(P)H peak 315 was the strongest one among the intensities of four NAD(P)H peaks 315, 325, 335 and 345. For the cells at the subsequent second stage that were treated for 1 minute, the intensity of the NAD(P)H peak 325 decreased in comparison to the intensity of the NAD(P)H peak 315. The intensity of the NAD(P)H peak 335 further decreased for the cells at the subsequent third stage that were treated for 5 minutes. For the cells at the subsequent fourth stage that were treated for 10 minutes, the intensity of the NAD(P)H peak 345 was the weakest one among the intensities of four NAD(P)H peaks 315, 325, 335 and 345. None of the heating treated SW480 cells re-grow in the follow-up cell proliferation study.

According to the present invention, the intensity decrease of the NAD(P)H signal peak of the fluorescent spectra at wavelength around 460 nm from the illuminated cells was identified as a response of the illuminated cells to cellular stress and preceding the development of phenotypic changes characteristic of cell death by hours to days. The intensity decrease of the NAD(P)H signal peak of the fluorescent spectra was a spectroscopic signature of the early stages of apoptosis of the cells.

A follow-up cell survival study revealed an interesting behavior of the heating treated cells. In the case of which the cells were treated with low-temperature heating, the result showed that, although many cells suffered irreversible thermal damage (oncosis), some treated cells were able to attach to the bottom of the petri dish during the initial re-growing process. These cells, however, did not proliferate 72 hours after the heating treatment (not shown here) and eventually released themselves from into the culture media. These cells not immediately killed by the heating were experiencing apoptosis.

Now referring to FIG. 4, the fluorescent spectra emitted from human colon adenocarcinoma cells (SW480) at different stages of apoptotic death were shown, where the SW480 cells were treated with cisplatin (hereinafter "CDDP") (100 microg/ml) for three-hour. Specifically, spectrum curve 410 was corresponding to the fluorescence spectrum of the cells soon after the three-hour CDDP treatment, with a NAD(P)H peak 415 at the wavelength around 460 nm. Spectrum curve 420 was the fluorescence spectrum of the cells 12 hours after the three-hour CDDP treatment, with a NAD(P)H peak 425 at the wavelength around 460 nm. Spectrum curve 430 was the fluorescence spectrum of the cells 24 hours after the three-hour CDDP treatment, with a NAD(P)H peak 435 at the wavelength around 460 nm. And spectrum curve 440 was corresponding to the fluorescence spectrum of the cells 48 hours after the three-hour CDDP treatment, with a NAD(P)H peak 445 at the wavelength around 460 nm. As shown in FIG. 4, the intensity of the NAD(P)H peak 425 of spectrum curve 420 for the cells 12 hours after the three-hour CDDP treatment decreased from the intensity of the NAD(P)H peak 415 of spectrum curve 410 for the cells soon after the three-hour CDDP treatment. En the case of which the cells were at 24 hours after the three-hour CDDP treatment, however, the intensity of the NAD(P)H peak 435 of spectrum curve 430 increased in comparison to the intensity of the NAD(P)H peak 425 of spectrum curve 420 for the cells 12 hours after the three-hour CDDP treatment, but still was less than the intensity of the NAD(P)H peak 415 for the cells soon after the three-hour CDDP treatment. For a longer time, for example, 48 hours after the three-hour CDDP treatment, the intensity of the NAD(P)H peak 445 of spectrum curve 440 of the cells dramatically decreased.

Figure 5:
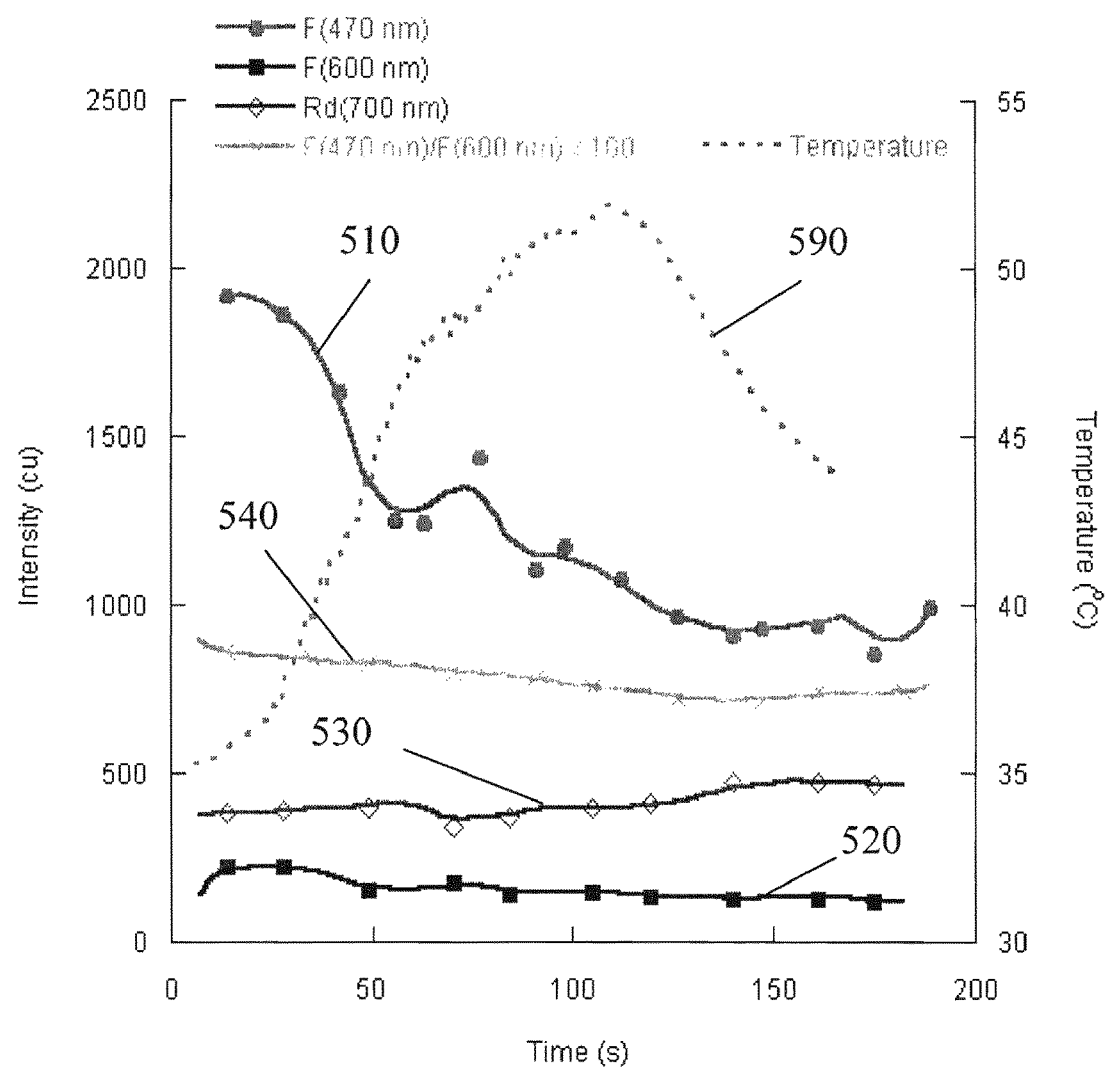
FIG. 5 shows dynamics of optical spectral features of liver tissues undergoing radio frequency ablation.

Referring now to FIG. 5, dynamics of fluorescence and diffused reflectance spectral feature of liver tissues undergoing a RFA were shown according one embodiment of the present invention. Fluorescence intensity curve 510 was acquired at a wavelength around 470 nm, which was very close to a NAD(P)H signal wavelength, 460 nm. Fluorescence intensity curve 520 was acquired at a wavelength around 600 nm. Curve 540 was a ratio of the fluorescence intensity 510 at the wavelength around 470 nm to the fluorescence intensity 520 at the wavelength around 600 nm. However, curve 530 was corresponding to a diffused reflectance intensity at the wavelength around 700 nm. The temperature-time history curve 590 from the same area where the optical spectra were acquired was also shown in FIG. 5. As shown in FIG. 5, the fluorescence intensity 510 from the liver tissues at a wavelength around 470 nm decreased significantly as the RFA operated, that was the liver tissues continuously suffered from heating. In the same situation, however, the changes of the fluorescence intensity 520 at the wavelength around 600 nm were much less significantly than the changes of the fluorescence intensity 510 at the wavelength around 470 nm as the liver tissues continuously suffered from heating (i.e., RFA). Similarly, the diffused reflectance intensity 530 at the wavelength around 700 nm also changed very little as the radiofrequency ablation operated. Therefore, the spectroscopic signature of which the intensity of fluorescence at a wavelength around the NAD(P)H signal wavelength 460 nm decreases can be used for diagnosing apoptosis of cells or tissues of a living subject in an early stage and detecting death process of the cells or tissues of the living subject.

Example 2

In Vitro Liver Tissue Discrimination

In one embodiment, liver samples, including normal and malignant liver tissues, were obtained from patients receiving a hepatic tumor resection and liver transplant. The liver samples were stored in a freezer at about −80° C. if not used immediately. The frozen liver samples were passively thawed at room temperature for at least 30 minutes prior to the optical spectral data collections.

Fluorescence emission characteristics of the normal and malignant liver tissues were characterized with excitation of a coherent light having a wavelength from about 250 nm to about 550 nm in about 10 nm increments using a spectrofluorometer, such as a LS-50 (Perkin Elmer Inc., Shelton, Conn.). The fluorescence spectra collected from a single sample were then used to form an excitation-emission matrix (hereinafter "EEM"). The liver samples of the normal and malignant liver tissues were dissected into about 5 mm thick slabs with a surface area larger than the spot size of the excitation light (i.e., about 3×8 mm$^2$) of the spectrofluorometer. Each prepared sample was inserted into a triangular quartz cell, Stama Cells (Stama Inc., Atascadero, Calif.) and then placed into the sample compartment of the spectrofluorometer to measure its EEM. Upon completing the spectral collection, comparisons were made among all EEMs recorded. Specifically, the peak locations and line-shape features, e.g., full-width half maximum (hereinafter "FWHM"), of major fluorescence emission peaks were identified from each EEM, these characteristics being then compared among samples. Absolute intensity information was not utilized in the analysis as it might be altered by factors other than tissue intrinsic characteristics, such as instrument performance. Through the empirical EEM analysis, the fluorescence characteristics of various liver tissue types were revealed.

Figure 6:
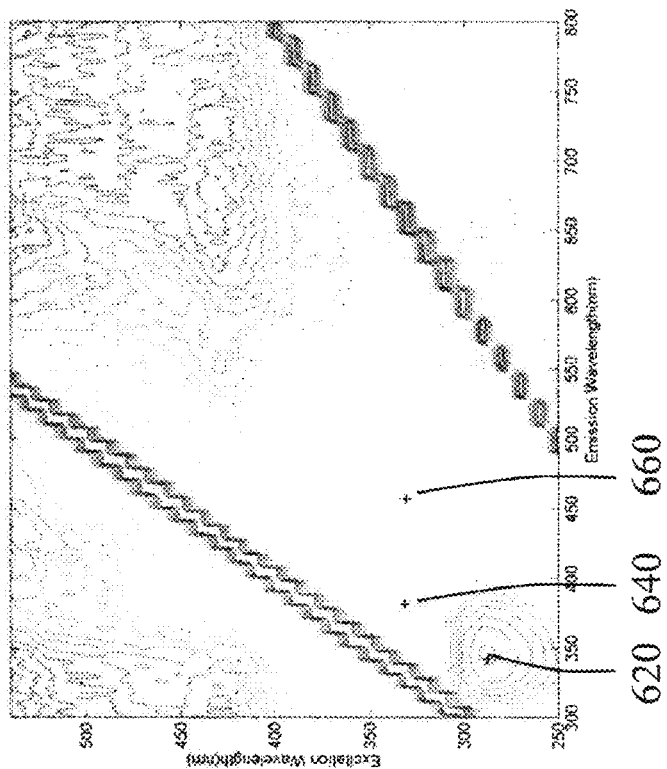
FIG. 6 shows in vitro an excitation-emission matrix of fluorescence spectra: (a) from a normal liver tissue, and (b) from a colon metastasis liver tissue.
Figure 6:
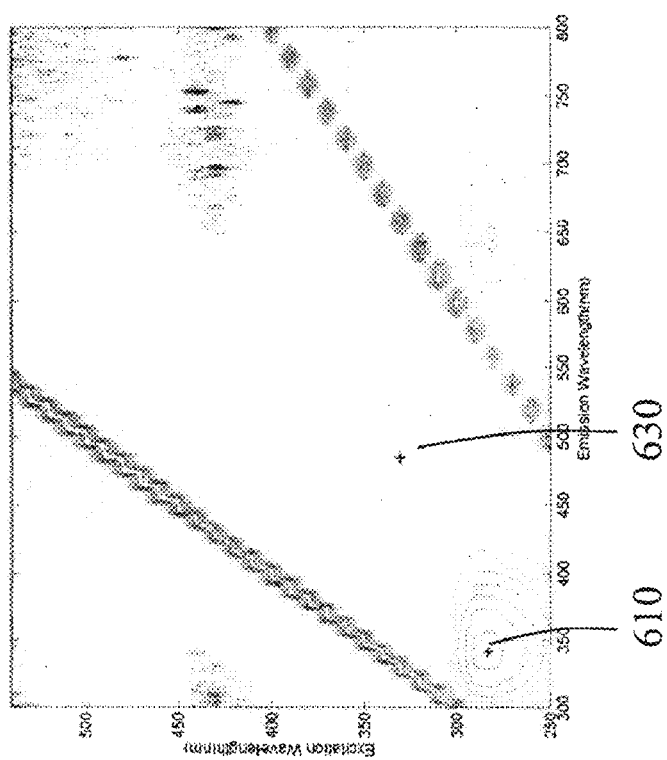

Referring to FIG. 6, EEM were shown for normal liver and colon metastasis liver tissues. The EEM measurement was performed on seven liver samples from four different patients. These seven liver samples included three normal liver samples, two liver tumors, and two cirrhotic tissues. All of the EEMs acquired, except one from a normal liver, showed two major fluorescence emission peaks: one at about 280 nm excitation, about 345 nm emission, and the other at about 330 nm excitation, about 470 nm emission. The corresponding fluorescence emission peaks were indicated by crosses 610 and 630, respectively, in FIG. 6a for the normal liver tissues, and by crosses 620 and 660, respectively, in FIG. 6b for the malignant liver tissues. The intensity of the fluorescence emission peak at crosses 610 (620) was found to be much more intense than that of the fluorescence emission peak at crosses 630 (660). In addition, the cirrhotic tissue and liver tumor samples also possessed a third peak at about 330 nm excitation, about 380 nm emission, as indicated by cross 640 in FIG. 6b. This peak 640 was especially pronounced in the tumor samples with necrosis. Due to the existence of this peak 640 in malignant liver tissues, 330±10 nm was chosen as ideal excitation wavelengths for liver tissue discrimination using fluorescence spectroscopy.

In vitro fluorescence and diffused reflectance spectra from liver tissues were further characterized using a fiberoptical spectroscopy system shown in FIG. 2. An interrogation time of one second was used in all spectral acquisitions to achieve adequate signal to noise ratio. From each investigated site, baseline, fluorescence, and diffused reflectance spectra were sequentially acquired and stored in a computer associated with the processor 280 of FIG. 2. At least two sites were optically interrogated from each tissue sample. All in vitro fluorescence and diffused reflectance spectra were processed to eliminate the instrumentation-induced variations prior any comparisons were made. The fluorescence and diffused reflectance spectra can be also acquired in an alternative order.

Figure 7:
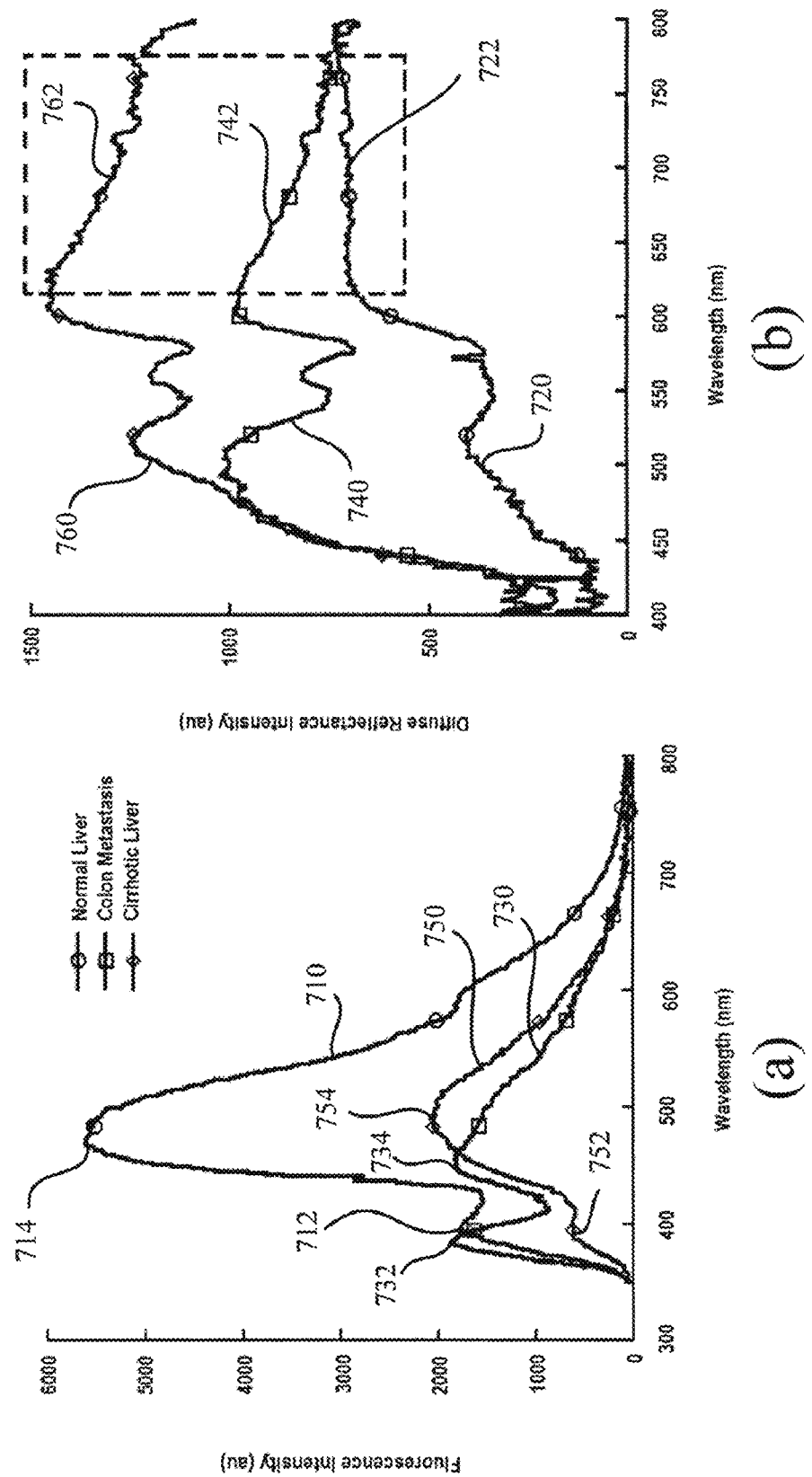
FIG. 7 shows in vitro optical spectra from different liver tissues: (a) fluorescence spectra, and (b) diffused reflectance spectra.

Eight human liver samples, including two cirrhotic liver tissues, three normal liver tissues, and three liver tumors (i.e., two colon metastasis and one primary liver tumor) were used in this practice of the present invention. In a preferable embodiment, liver samples were excited with a coherent light having a wavelength between about 320 nm and about 340 nm. As shown in FIG. 7a, fluorescence spectra varied significantly among different types of the liver tissue samples. In general, these fluorescence spectra had two fluorescence intensity peaks. The first peak wavelength $\lambda_1$ of the fluorescence spectrum was in a range of about 370 nm to about 400 nm, and the second peak wavelength $\lambda_2$ of the fluorescence spectrum was in a range of about 460 nm to about 500 nm. For example, all of the fluorescence spectra 710 acquired from the normal liver tissues showed one strong peak 714 at about $\lambda_2$=470 nm emission, the intensity of the fluorescence peak 714 varied between about 1900 au to about 5500 au resulting in a mean± standard deviation (hereinafter "SD"), about 2854±548 au, for n=7 different measurements. A peak 712 at about $\lambda_1$=395 nm emission was also found in the fluorescence spectra 710 from the normal liver tissues. A ration of the intensity of the first peak 712 at about $\lambda_1$=395 nm to the intensity of the second peak 714 at about $\lambda_2$=470 nm was much less than one. In addition, the blood-absorption-induced valleys at about 540 nm and about 580 nm emission were observed in the fluorescence spectra 710 acquired from several normal liver tissues.

As shown in FIG. 7a, the fluorescence spectra 750 acquired from the cirrhotic liver tissues were relatively similar to those from the normal liver tissues: two fluorescence intensity peaks 752 and 754 at about $\lambda_1$=395 nm and about $\lambda_2$=490 nm emission, respectively, and the ration of the intensity of the first peak 752 at about $\lambda_1$=395 nm to the intensity of the second peak 754 at about $\lambda_2$=490 nm was much less than one. The maximum fluorescence emission intensity from the cirrhotic liver tissues were about 1894±548 au, for n=4, which was smaller than that from the normal liver tissues. However, the FWHM of the second fluorescence emission peak 754 from the cirrhotic liver tissues, which was about 134±4 nm, for n=4, was greater than that of the fluorescence peak 714 from the normal liver tissues, which was about 121.3±4 nm, for n=7.

Fluorescence spectra 730 obtained from the liver tumor varied greatly in terms of their intensity as well as line-shape. All the fluorescence spectra 730 acquired from the tumor samples possessed a strong peak between about 450 nm and about 500 nm emission. Two of these fluorescence spectra showed three emission peaks at about 380 nm, about 430 nm, and about 500 nm, with the peak at about 380 nm emission being the strongest. The ratio of the fluorescence intensities of the first peak 732 at a wavelength about $\lambda_1$=380 nm and the second peak 734 at a wavelength about $\lambda_2$=480 nm of the fluorescence spectrum 730 from the liver tumors was about one or greater than one, which was generally greater than those of the normal liver tissues.

FIG. 7b shows diffused reflectance spectra acquired from the normal liver tissues and malignant liver tissues. For the normal liver tissues, the intensity 722 of the diffused reflectance spectrum 720 over a wavelength range from about 625 nm to and about 800 nm remained almost unchanged, and the blood absorption signature, corresponding to spectral valleys, appeared in the diffused reflectance spectrum 720 at wavelengths about 540 nm and about 580 nm. The diffused reflectance spectra 740 and 760 acquired from the liver tumors and cirrhotic liver tissues, respectively, showed an interesting trend between about 600 nm and about 800 nm emission. The intensity 742 (and 762) of the diffused reflectance spectrum 740 (and 760) was monotonically decreased over the predetermined wavelength region from about 600 nm to about 800 nm. In addition, the diffused reflectance intensities between 500 and 600 nm of the diffused reflectance spectra 740 and 760 from the liver tumors and cirrhotic liver tissues were substantially stronger than that of the diffused reflectance spectrum 720 from the normal liver tissues. These variations strongly suggest that liver tissue differentiation can be achieved using diffused reflectance spectroscopy.

Example 3

In Vivo Liver Tumor Differentiation

In vitro studies, small-scale human clinical trials were conducted at Vanderbilt University Medical Center. The experimental protocol for the clinical trials was approved by Vanderbilt Institution Review Board. Hepatic tumor patients receiving hepatic tumor resection were selectively recruited by a surgeon, according to the tumor sites and patient's medical condition. Prior to the clinical trials, the experimental procedures were carefully explained to the participants, and written consent was obtained from each of them.

In the clinical studies, fluorescence and diffused reflectance spectra were acquired from perfused (i.e., prior resection) and non-perfused (i.e., post resection) liver tissue using the fiberoptic spectroscopic system described above. The fiber optical probe was sterilized, so it could be used in the operating field. Once the liver of the studied patient was exposed, perfused fluorescence and diffused reflectance spectra were acquired from the normal liver and tumor exposed at the surface. The investigated sites were selected by the surgeon. The removed liver tissue was dissected to expose the tumor center. Then, optical spectral measurements were performed at tumor center, tumor margins, and surrounding normal liver tissues.

All the in vivo fluorescence and diffused reflectance spectra collected in this clinical study were pre-processed to remove the instrumentation-induced variations before any analyses were applied. In general, empirical comparisons of spectral intensities and line-shape between normal and tumor liver tissues were performed on the fluorescence and diffused reflectance spectra collected from each patient. As only limited patients have been studied to date, the spectral analysis was only performed within an individual patient.

Figure 8:
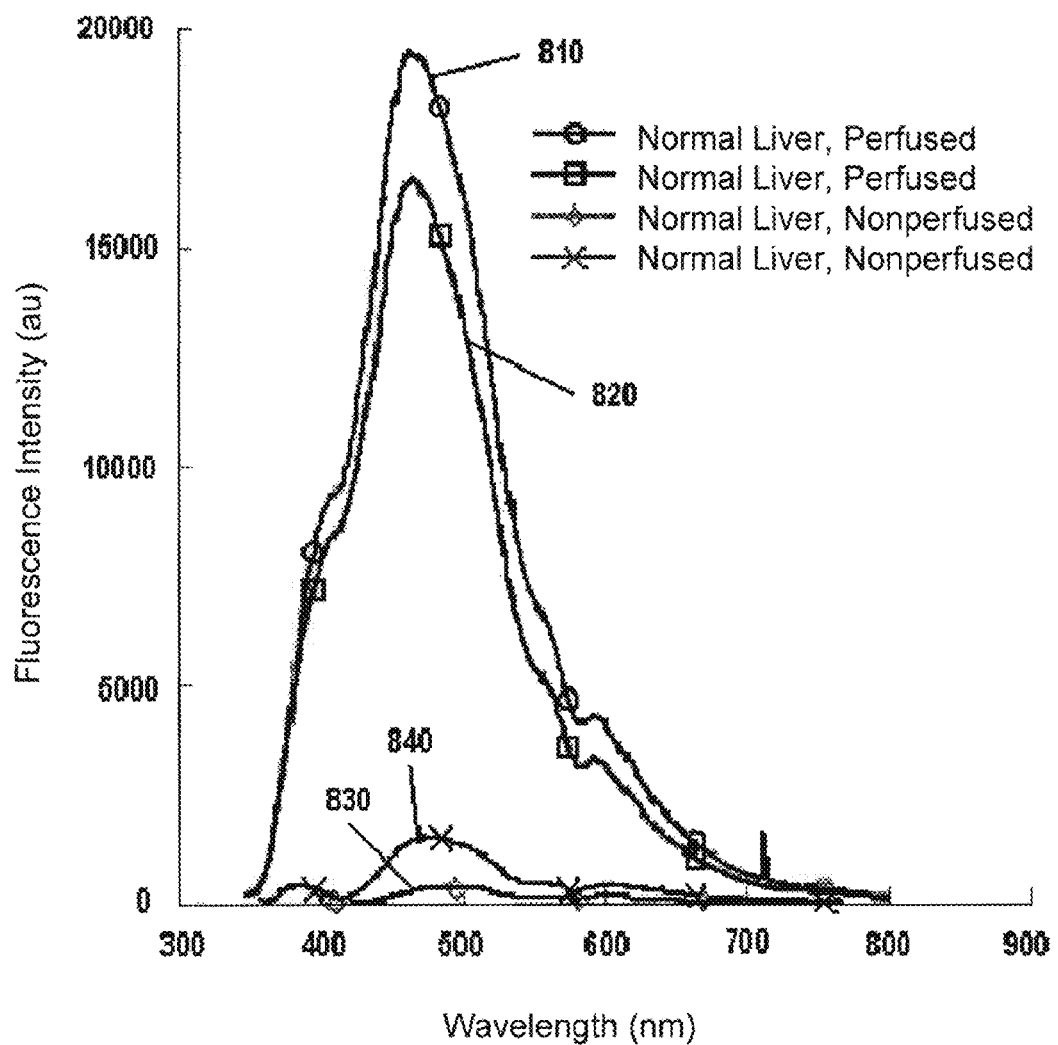
FIG. 8 shows in vivo fluorescence spectra from perfused and non-perfused liver tissues, respectively.

Referring to FIG. 8, in vivo spectral data collected from the normal liver tissues showed that the fluorescence spectra 810 and 820 from the perfused liver tissues were much more intense than those 830 and 840 from the non-perfused liver tissues. Their line-shapes of the fluorescence spectra 810, 820 830 and 840 were similar.

Figure 9:
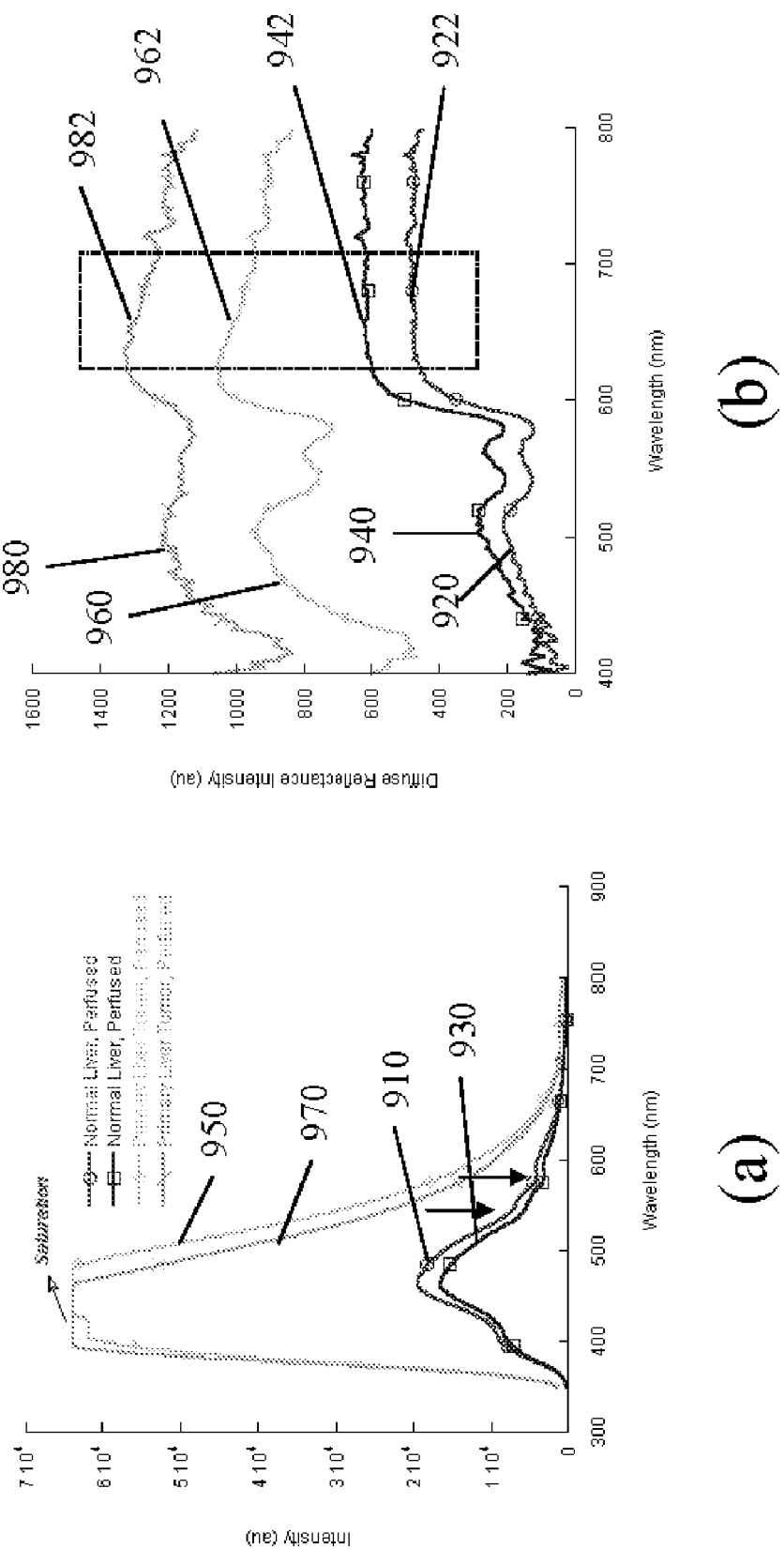
FIG. 9 shows in vivo optical spectra from normal liver tissues and primary liver tumors, respectively: (a) fluorescence spectra, (b) diffused reflectance spectra.

Referring to FIG. 9, fluorescence spectra 950 and 970 and diffused reflectance spectra 960 and 980 from a primary liver tumor patient were shown. For comparison, fluorescence spectra 910 and 930 and diffused reflectance spectra 920 and 940 from the normal liver tissues were also shown in FIG. 9. FIG. 9a showed that the fluorescence intensities between about 400 nm and about 650 nm emission from the primary liver tumors were very intense, and were at least three times greater than those from the normal liver tissues. In addition, the blood absorption optical signature, corresponding to spectral valleys at wavelengths about 540 nm and 580 nm, respectively, appeared in the fluorescence spectra 910 and 930 from the normal liver tissues, but not in those 950 and 970 from the primary liver tumors. FIG. 9b showed that the diffused reflectance intensities, represented by spectral curves 960 and 980, from the primary liver tumors were also greater than those (spectral curves 920 and 940) from the normal liver tissues. Moreover, the diffused reflectance intensity from the primary liver tumors decreased monotonically from 600 nm to 700 nm, while the diffused reflectance intensity from the normal liver tissues remained unchanged in this wavelength region. This observation concurred with that uncovered in the in vitro study described above.

Figure 10:
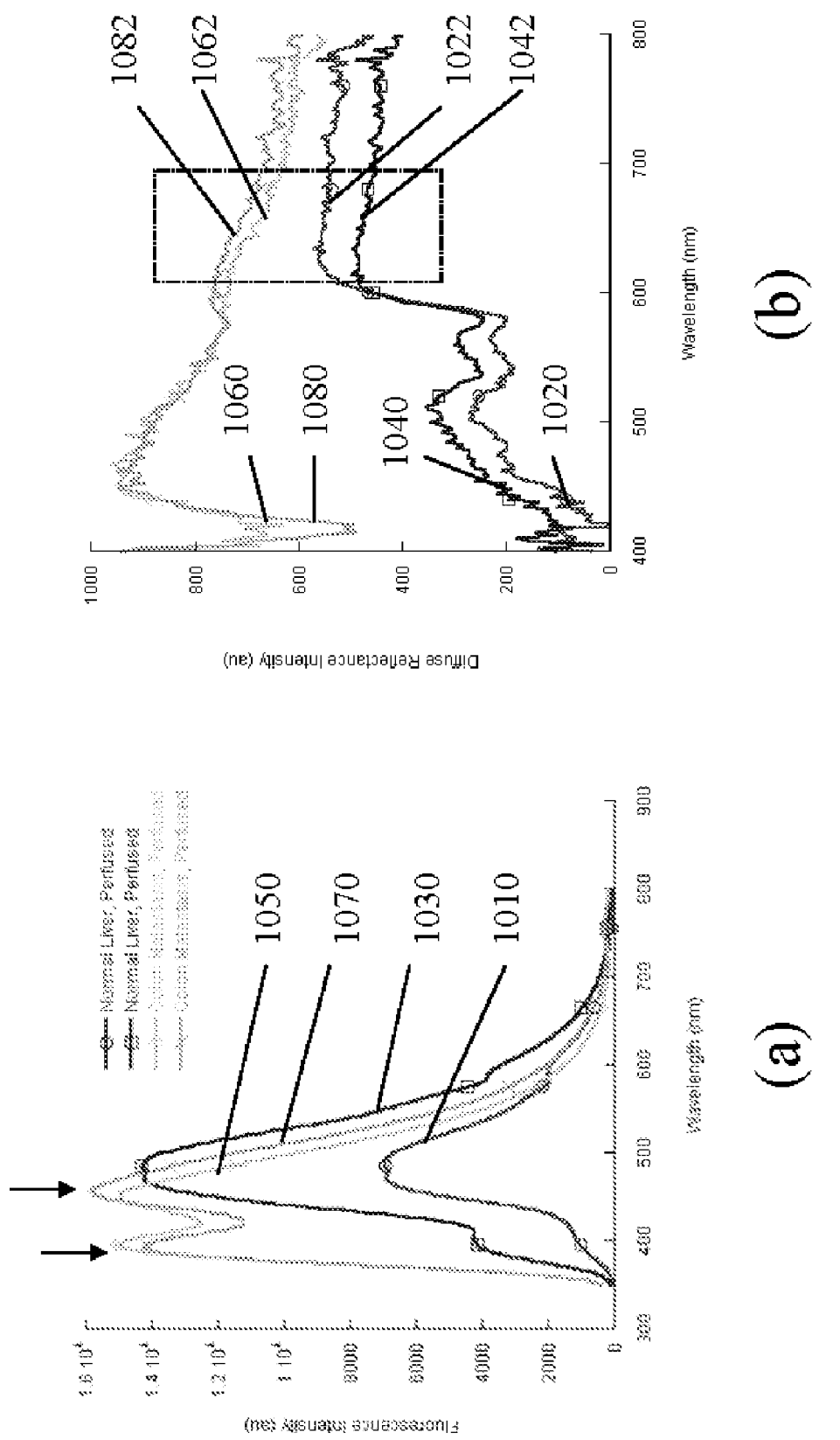
FIG. 10 shows in vivo optical spectra from normal liver tissues and secondary liver tumors, respectively: (a) fluorescence spectra, (b) diffused reflectance spectra.

Referring to FIG. 10, fluorescence and diffused reflectance spectra acquired from a secondary liver tumor (i.e., colon metastasis) patient were presented. FIG. 10 also showed fluorescence spectra 1010 and 1030 and diffused reflectance spectra 1020 and 1040 from the normal liver tissues. As shown in FIG. 10a, the most noticeable difference between the fluorescence spectra 1010 1030 from the normal liver tissues and those 1050 and 1070 from the colon metastasis was the line-shape. The fluorescence spectra 1050 and 1070 acquired from the colon metastasis had two pronounced peaks at wavelengths about 400 nm and about 480 nm emission, respectively, while the fluorescence spectra 1010 and 1030 from the normal liver tissues only possessed one broad emission peak with a wavelength between about 470 nm and about 500 nm. The intensities of the diffused reflectance spectra 1060 and 1080 from the colon metastasis were greater than those 1040 and 1040 from the normal liver tissues. Moreover, the diffused reflectance intensities 1062 and 1082 from the colon metastasis decreased monotonically over a wavelength region from about 600 nm to about 700 nm, while the diffused reflectance intensities 1022 and 1042 from the normal liver tissues remained relatively unchanged over the wavelength region.

With respect to the order of acquiring fluorescence and diffused reflectance spectra, there is no preference for successfully practicing the present invention. One can acquire either of them first; or alternatively, one can acquire both substantially at the same time.

While there has been shown various embodiments of the present invention, it is to be understood that certain changes can be made in the form and arrangement of the elements of the apparatus and steps of the methods to practice the present invention as would be known to one skilled in the art without departing from the underlying scope of the invention which is defined by the specification, the claims and drawings. For examples, while examples set forth above are related to practice the present invention in a human, the present invention can be practiced in an animal as well. The coherent light may be emitted from a light source other than a laser light source. Furthermore, the embodiments described above are only intended to illustrate the principles of the present invention and are not intended to limit the invention to the disclosed elements.

What is claimed is:

1. A method for differentiating malignant in vivo liver tissues from normal in vivo liver tissues of a living subject, comprising the steps of:
    (a) illuminating a first area and a second area of in vivo liver tissues of the living subject with a first excitation light;
    (b) measuring an intensity of fluorescent light emitted from the first area of in vivo liver tissues and an intensity of fluorescent light emitted from the second area of in vivo liver tissues in response to the first excitation light as a function of wavelength so as to obtain a first and a second fluorescent spectra of the in vivo liver tissues of the first area and the second area, respectively;
    (c) illuminating the first area and the second area of in vivo liver tissues of the living subject with a second excitation light;
    (d) measuring an intensity of diffuse light reflected by the first area of in vivo liver tissues and an intensity of diffuse light reflected by the second area of in vivo liver tissues in response to the excitation light as a function of wavelength so as to obtain a first and a second diffused reflectance spectra of the in vivo liver tissues of the first area and the second area, respectively; and
    (e) identifying one of the first area and the second area of in vivo liver tissues as malignant liver tissues and the other one of the first area and the second area of in vivo liver tissues as normal liver tissues, by identifying corresponding blood absorption signature through comparing the first fluorescence spectrum of the in vivo liver tissues of the first area and the second florescence spectrum of the in vivo liver tissues of the second area, and comparing the first diffused reflectance spectrum of the in vivo liver tissues of the first area and the second diffused reflectance spectrum of the in vivo liver tissues of the second area, wherein the fluorescence spectrum of the malignant liver tissues shows no blood absorption signature at a first wavelength of about 540 nm and a second wavelength of about 580 nm, and the intensity of the diffused reflectance spectrum of the malignant liver tissues substantially monotonically decreases over a wavelength region from about 620 nm to about 700 nm, and the fluorescence spectrum of the normal liver tissues shows blood absorption signature at the first wavelength of about 540 nm and the second wavelength of about 580 nm, and the intensity of the diffused reflectance spectrum of the normal liver tissues is substantially unchanged over the wavelength region from about 620 nm to about 700 nm, wherein the blood absorption signature in the fluorescence spectrum of the normal liver tissues corresponds to spectral valleys at the first wavelength of about 540 nm and the second wavelength of about 580 nm.

2. The method of claim 1, wherein the malignant liver tissues are identified as primary liver tumor tissues when the intensity of the fluorescence spectrum of the malignant liver tissues is at least three times larger than the intensity of the fluorescence spectrum of the normal liver tissues over a wavelength range of about 400 nm to about 600 nm.

3. The method of claim 1, wherein the malignant liver tissues are identified as secondary liver tumor tissues when the fluorescence spectrum of the malignant liver tissues has a first peak at a wavelength of about 400 nm and a second peak at a wavelength of about 480 nm, and a ratio of a corresponding first peak intensity to a corresponding second peak intensity is substantially about one.

4. The method of claim 1, wherein the first excitation light is substantially monochromatic and has a dominant wavelength between about 320 nm and about 340 nm.

5. The method of claim 1, wherein the second excitation light is substantially white light.

6. An apparatus for differentiating malignant in vivo liver tissues from normal in vivo liver tissues of a living subject, comprising:
    (a) a first light source adapted for emitting a first excitation light;
    (b) a second light source adapted for emitting a second excitation light;
    (c) a fiber optical probe coupled with the first light source and the second light source and configured to deliver the first excitation light and the second excitation light to a first area of in vivo liver tissues of the living subject in a first instance, and to deliver the first excitation light and the second excitation light to a second area of in vivo liver tissues of the living subject in a second instance;
    (d) a detector coupled with the fiber optical probe and configured to receive fluorescent light emitted from and diffuse light reflected by the first area of in vivo liver tissues of the living subject in response to the first excitation light and the second excitation light, respectively, in the first instance, and to measure an intensity of the fluorescent light emitted from the first area as a function of wavelength, and an intensity of the diffuse light reflected by the first area as a function of wavelength, so as to obtain a first fluorescent spectrum of the first area, and a first diffused reflectance spectrum of the first area, respectively, the detector is further configured to receive fluorescent light emitted from and diffuse light reflected by the second area of the living subject in response to the first excitation light and the second excitation light, respectively, in the second instance, and to measure an intensity of the fluorescent light emitted from the second area as a function of wavelength, and an intensity of the diffuse light reflected by the second area as a function of wavelength, so as to obtain a second fluorescent spectrum of the second area, and a second diffused reflectance spectrum of the second area, respectively; and
    (e) a controller coupled with the detector and programmed to identify corresponding blood absorption signature through comparing the first fluorescence spectrum of the in vivo liver tissues of the first area and the second fluorescence spectrum of the in vivo liver tissues of the second area, and to compare the first diffused reflectance spectrum of the in vivo liver tissues of the first area and the second diffused reflectance spectrum of the in vivo liver tissues of the second area, so as to identify one of the first area and the second area of in vivo liver tissues as malignant liver tissues and the other one of the first area and the second area of in vivo liver tissues as normal liver tissues, wherein the fluorescence spectrum of the malignant liver tissues does not show blood absorption signature at a first wavelength of about 540 nm, and at a second wavelength of about 580 nm, and the intensity of the diffused reflectance spectrum of the malignant tissues substantially monotonically decreases over a wavelength region from about 620 nm to about 700 nm, and the fluorescence spectrum of the normal liver tissues shows blood absorption signature at the first wavelength of about 540 nm and the second wavelength of about 580 nm, and the intensity of the diffused reflectance spectrum of the normal liver tissues is substantially unchanged over the wavelength region from about 620 nm to about 700 nm, wherein the blood absorption signature in the fluorescence spectrum of the normal liver tissues corresponds to spectral valleys at the first wavelength of about 540 nm and the second wavelength of about 580 nm.

7. The apparatus of claim 6, wherein the first light source comprises a laser, and the first excitation light has substantially a wavelength between about 320 nm and about 340 nm.

8. The apparatus of claim 6, wherein the second light source comprises a halogen light source.

9. The apparatus of claim 6, wherein the detector comprises a spectrometer.

10. The apparatus of claim 6, wherein the controller comprises a computer.

\* \* \* \* \*